(12) United States Patent
Schmidt et al.

(10) Patent No.: US 6,557,549 B2
(45) Date of Patent: May 6, 2003

(54) AEROSOL DELIVERY APPARATUS WITH POSITIVE EXPIRATORY PRESSURE CAPACITY

(75) Inventors: James N. Schmidt, London (CA); Daniel Engelbreth, London (CA); Rick Blacker, London (CA)

(73) Assignee: Trudell Medical International, London (CA)

( * ) Notice: Subject to any disclaimer, the term of this patent is extended or adjusted under 35 U.S.C. 154(b) by 80 days.

(21) Appl. No.: 09/833,019

(22) Filed: Apr. 11, 2001

(65) Prior Publication Data

US 2002/0029779 A1 Mar. 14, 2002

Related U.S. Application Data

(60) Provisional application No. 60/196,555, filed on Apr. 11, 2000.

(51) Int. Cl.[7] .................. A61M 15/00; A61M 16/00; A62B 9/00
(52) U.S. Cl. ................ 128/200.24; 128/205.23
(58) Field of Search .............. 128/200.24, 200.14, 128/200.22, 200.23, 203.12, 205.23, 204.23

(56) References Cited

U.S. PATENT DOCUMENTS

| 393,869 A | 12/1888 | Warren |
|---|---|---|
| 2,670,739 A | 3/1954 | McNeill |
| 4,182,366 A | 1/1980 | Boehringer |

(List continued on next page.)

FOREIGN PATENT DOCUMENTS

| EP | 0 372 148 A1 | 6/1990 |
|---|---|---|
| EP | 0 678 306 A2 | 10/1995 |
| EP | 0 938 908 A2 | 9/1999 |
| WO | WO 99/16490 | 4/1999 |
| WO | WO 00/27455 | 5/2000 |

OTHER PUBLICATIONS

Copy of International Search Report for PCT/IB01/00599 dated Nov. 9, 2001.
E.F. Christensen et al., "Treatment of Bronchial Asthma with Terbutaline Inhaled by Conespacer Combined With Positive Expiratory Pressure Mask", Chest 100, vol. 2, 1991, pp 317–321.
J.B. Andersen et al., "A new Mode of Administration of Nebulized Bronchodilator in Severe Bronchospasm", Eur J Respir Dis Suppl 119, vol. 63, 1982, pp 97–100.
R. Wilson, "Positive Expiratory Pressure Therapy: The Key to Effective, Low–Cost Removal of Bronchial Secretions", The Journal for Respiratory Care Practitioners, Mar. 1999, pp 67–68.
M.J. Mahlmeister et al., "Positive–Expiratory–Pressure Mask Therapy: Theoretical and Practical Considerations and a Review of the Literature", Respiratory Care Nov. 1991, vol. 36, No. 11, pp 1218–1229.
"Technology Showcase Adjuncts to Bronchial Hygiene Therapy", AARC Times, May 1998, 2 pages.
"AARC Clinical Practice Guideline: Use of Positive Airway Pressure Adjuncts to Bronchial Hygiene Therapy", Respiratory Care, May 1993, vol. 38 No. 5, pp 516–520.

(List continued on next page.)

Primary Examiner—Henry Bennett
Assistant Examiner—Alfred Basichas
(74) Attorney, Agent, or Firm—Brinks Hofer Gilson & Lione

(57) ABSTRACT

An apparatus and method for performing positive pressure (PP) therapy alone or in combination with an aerosol delivery apparatus. The positive pressure apparatus includes a positive pressure valve having a continuously variable respiratory window. The PP valve may be associated with a patient respiratory system interface alone, such as, but not limited to, a mask or mouthpiece, or in combination with an aerosol delivery apparatus.

32 Claims, 17 Drawing Sheets

U.S. PATENT DOCUMENTS

| | | | |
|---|---|---|---|
| 4,231,375 A | | 11/1980 | Boehringer et al. |
| 4,267,832 A | | 5/1981 | Häkkinen |
| 4,275,722 A | * | 6/1981 | Sorensen ............... 128/200.24 |
| 4,298,023 A | | 11/1981 | McGinnis |
| 4,470,412 A | | 9/1984 | Nowacki et al. |
| 4,635,631 A | * | 1/1987 | Izumi .................... 128/204.23 |
| 4,770,413 A | | 9/1988 | Green |
| 4,981,295 A | | 1/1991 | Belman et al. |
| 5,042,467 A | | 8/1991 | Foley |
| 5,193,529 A | * | 3/1993 | Labaere ................. 128/200.24 |
| 5,479,920 A | * | 1/1996 | Piper et al. ............ 128/204.23 |
| 5,598,839 A | | 2/1997 | Niles et al. |
| 5,645,049 A | | 7/1997 | Foley et al. |
| 5,647,345 A | * | 7/1997 | Saul ...................... 128/201.23 |
| 5,658,221 A | | 8/1997 | Hougen |
| 5,848,588 A | | 12/1998 | Foley et al. |
| 5,890,998 A | | 4/1999 | Hougen |
| 5,899,832 A | | 5/1999 | Hougen |
| 5,925,831 A | | 7/1999 | Storsved |
| 6,026,807 A | | 2/2000 | Puderbaugh et al. |
| 6,044,841 A | | 4/2000 | Verdum et al. |
| 6,089,105 A | | 7/2000 | Ricciardelli |
| 6,240,917 B1 | | 6/2001 | Andrade |
| 6,293,279 B1 | | 9/2001 | Schmidt et al. |
| 6,345,617 B1 | | 2/2002 | Engelbreth et al. |
| 6,412,481 B1 | | 7/2002 | Bienvenu et al. |

OTHER PUBLICATIONS

J.L. Rau et al., "Combining a Positive Expiratory Pressure Device with a Metered–Dose Inhaler Reservoir System Using Chlorofluorocarbon Albuterol and Hydrofluoroalkane Albuterol: Effect on Dose and Particle Size Distributions", Respiratory Care, Mar. 2000, vol. 45 No. 3, pp 320–326.

Copy of pamphlet for "TheraPEP: Positive Expiratory Pressure Therapy System", Catalog No. 20–1112, published prior to Apr. 11, 2001, 4 pages.

Copy of pamphlet for "PARI PEP System", Part No. 18F61, published prior to Apr. 11, 2001, 4 pages.

Copy of application as filed for U.S. Ser. No. 09/287,997 Filed: Apr. 7, 1999.

Copy of claims as filed for U.S. application Ser. No. 09/938,686 Filed: Jun. 12, 2000.

* cited by examiner

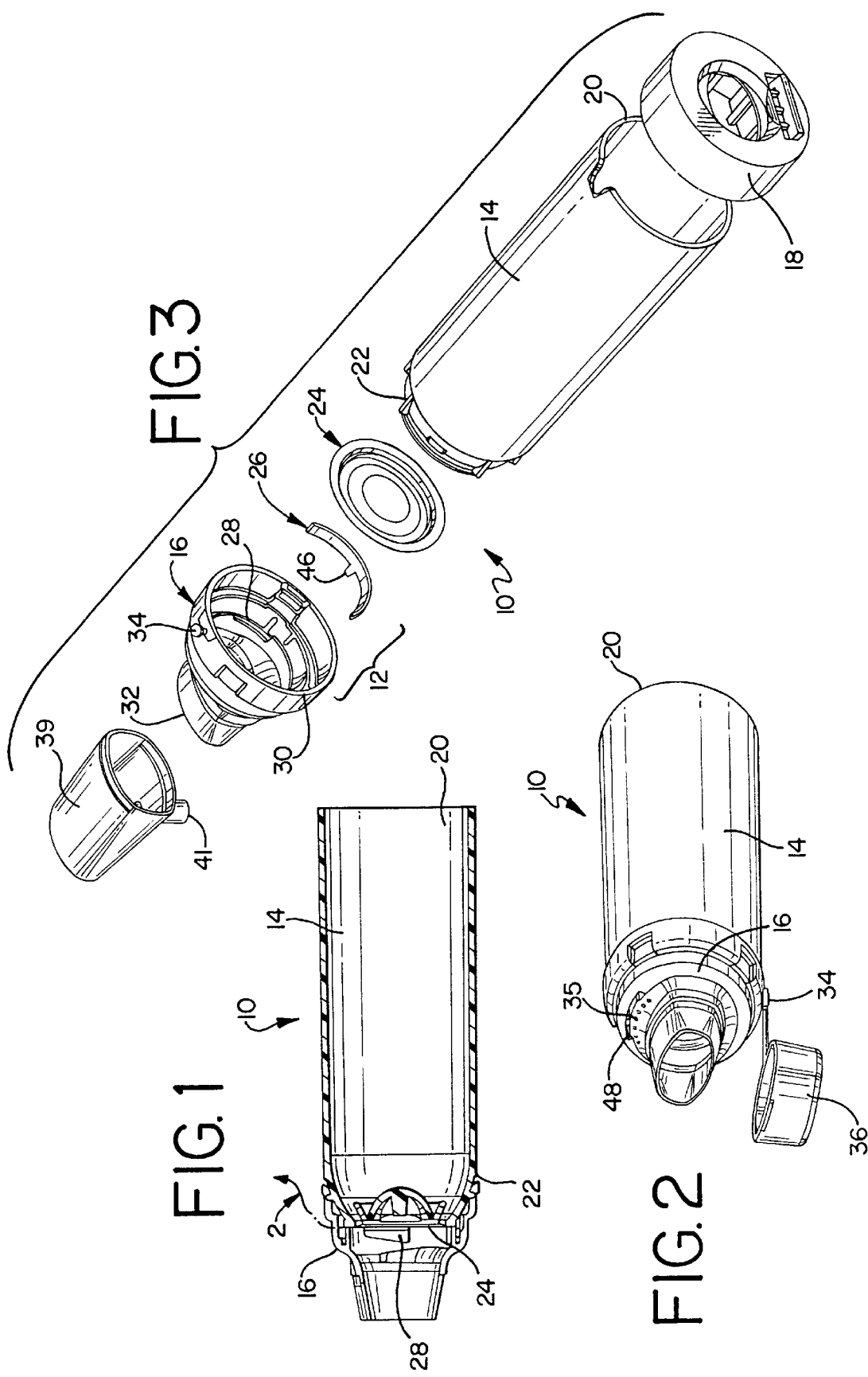

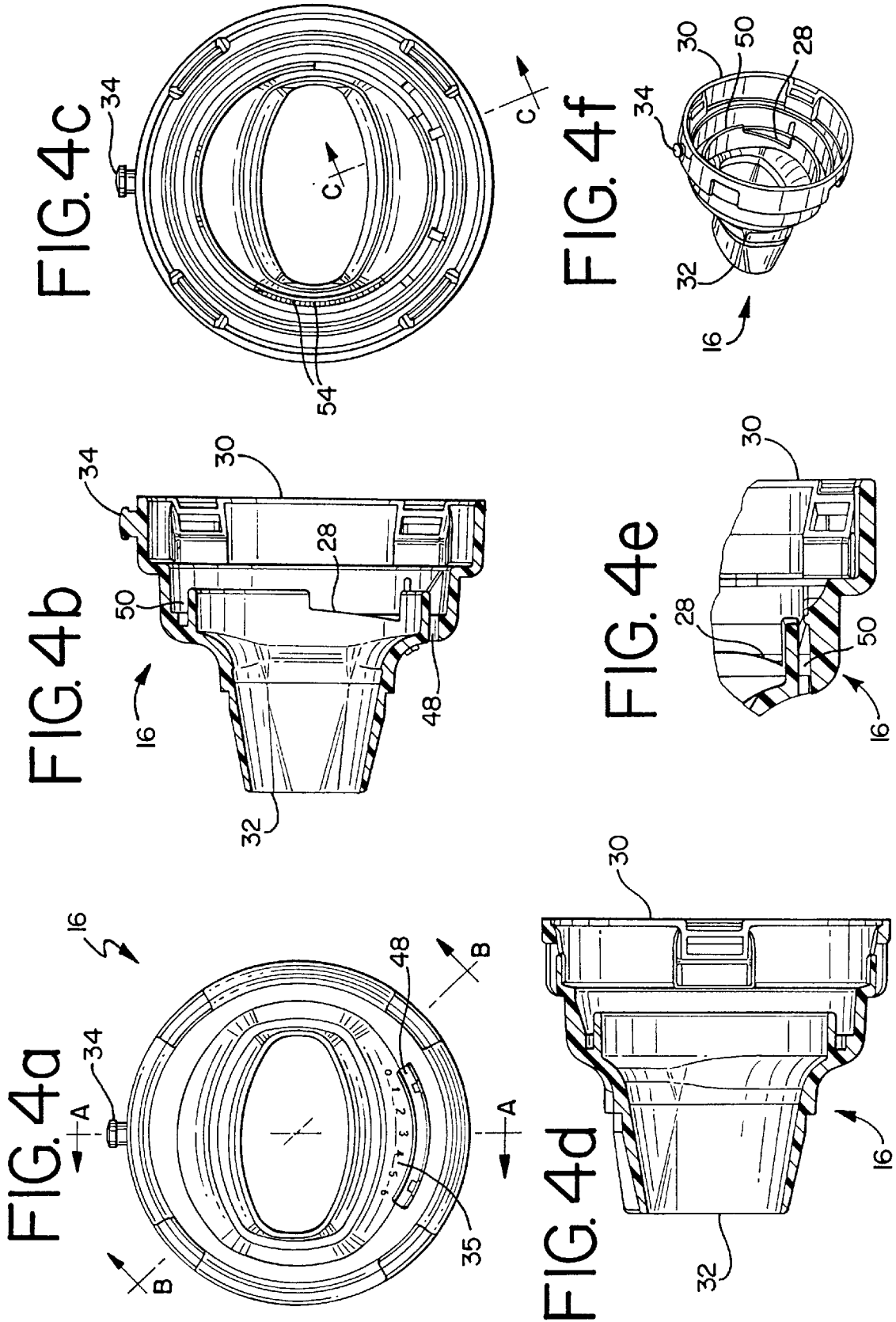

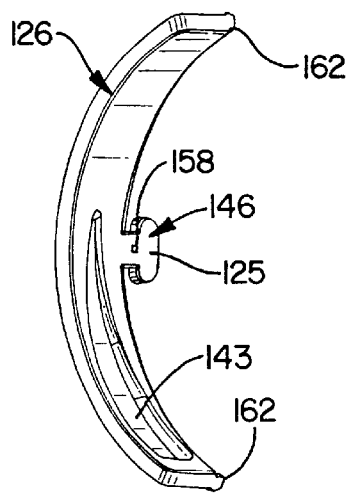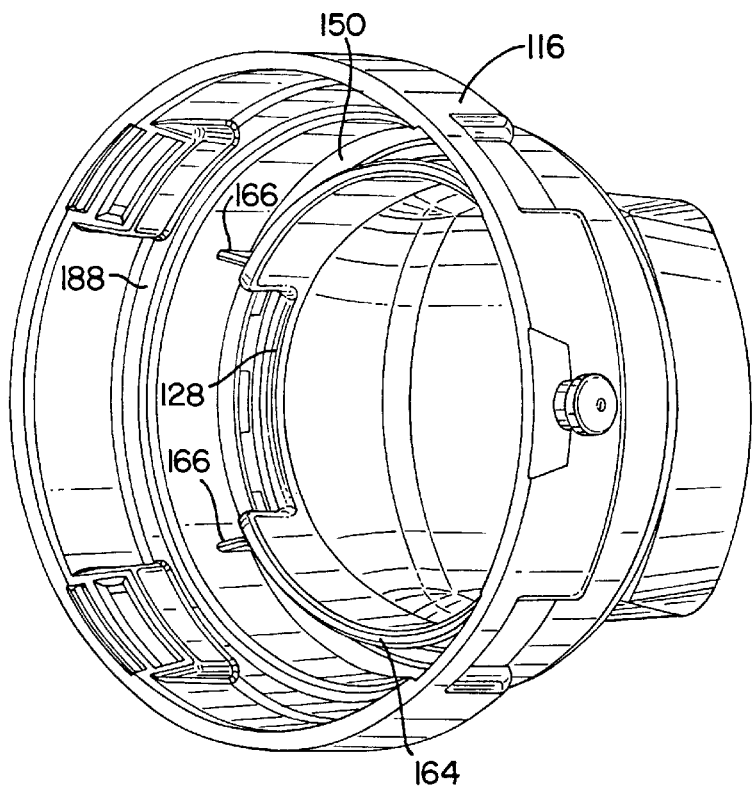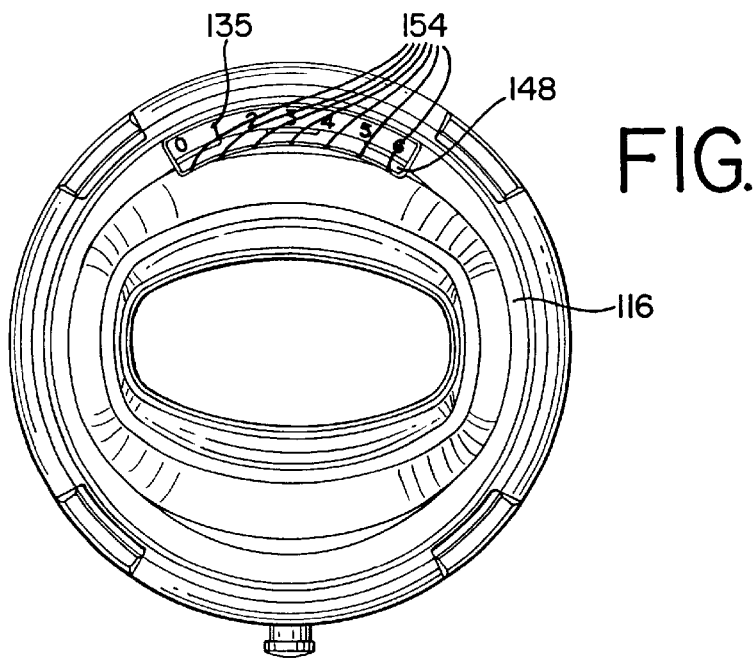

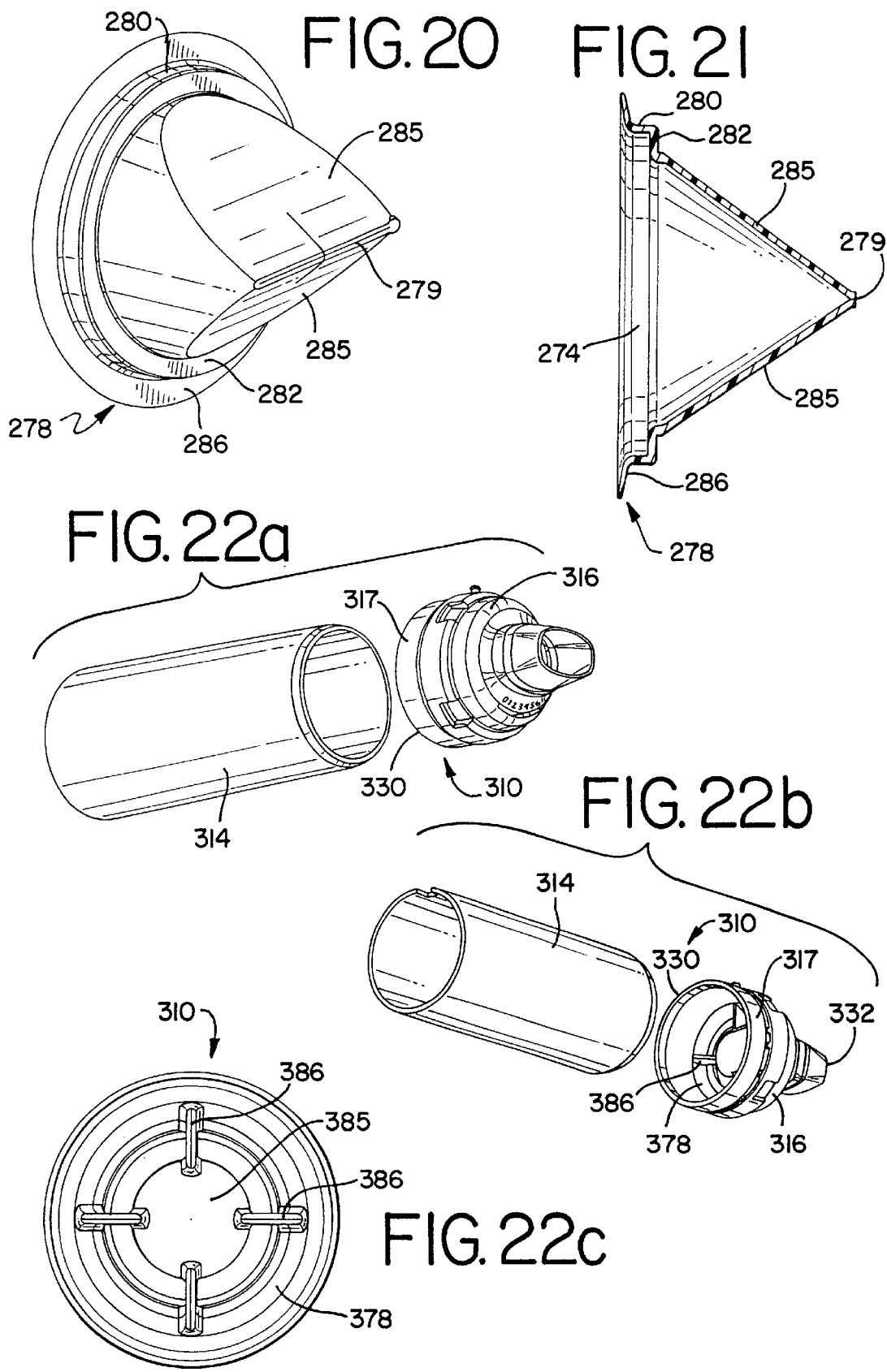

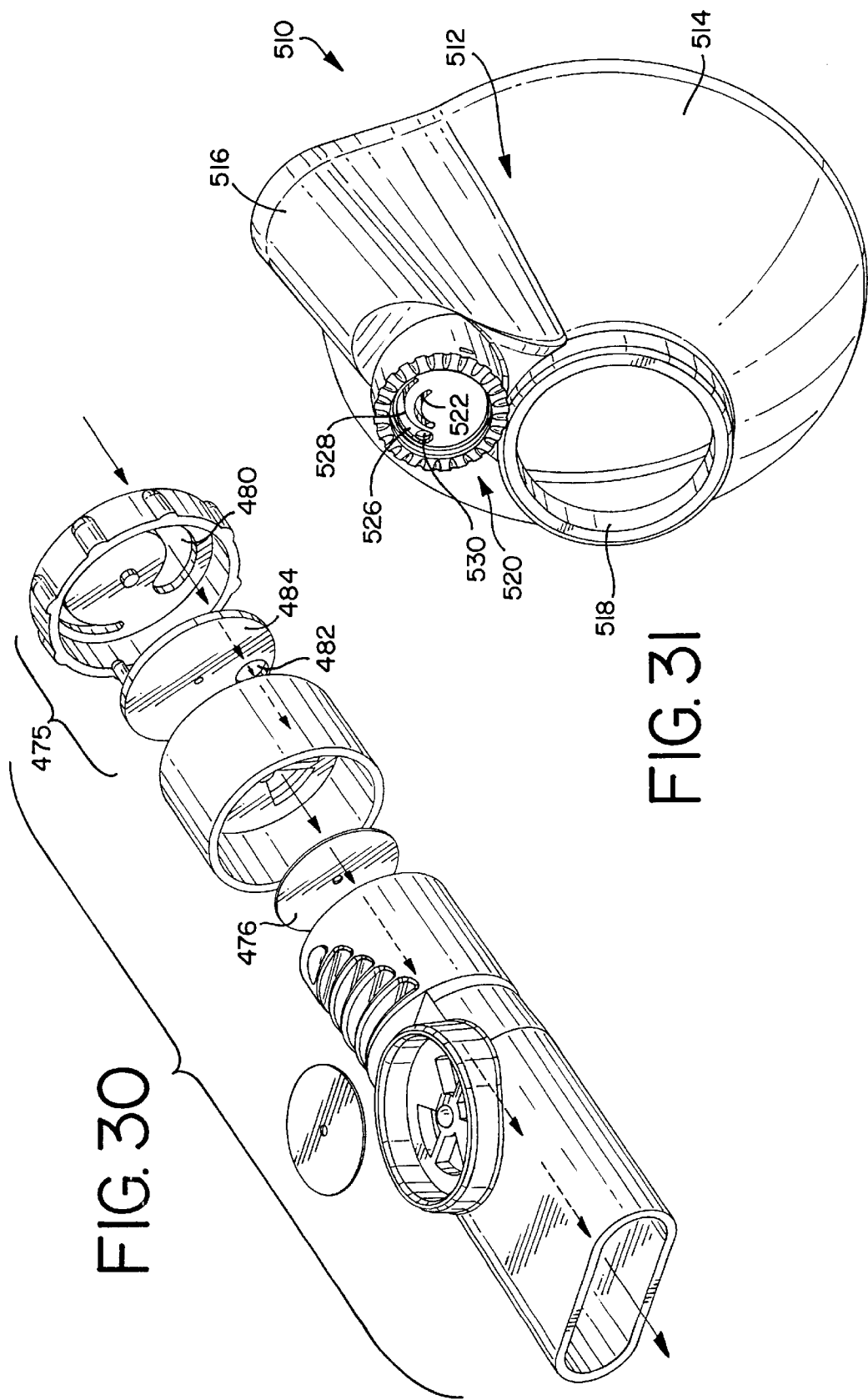

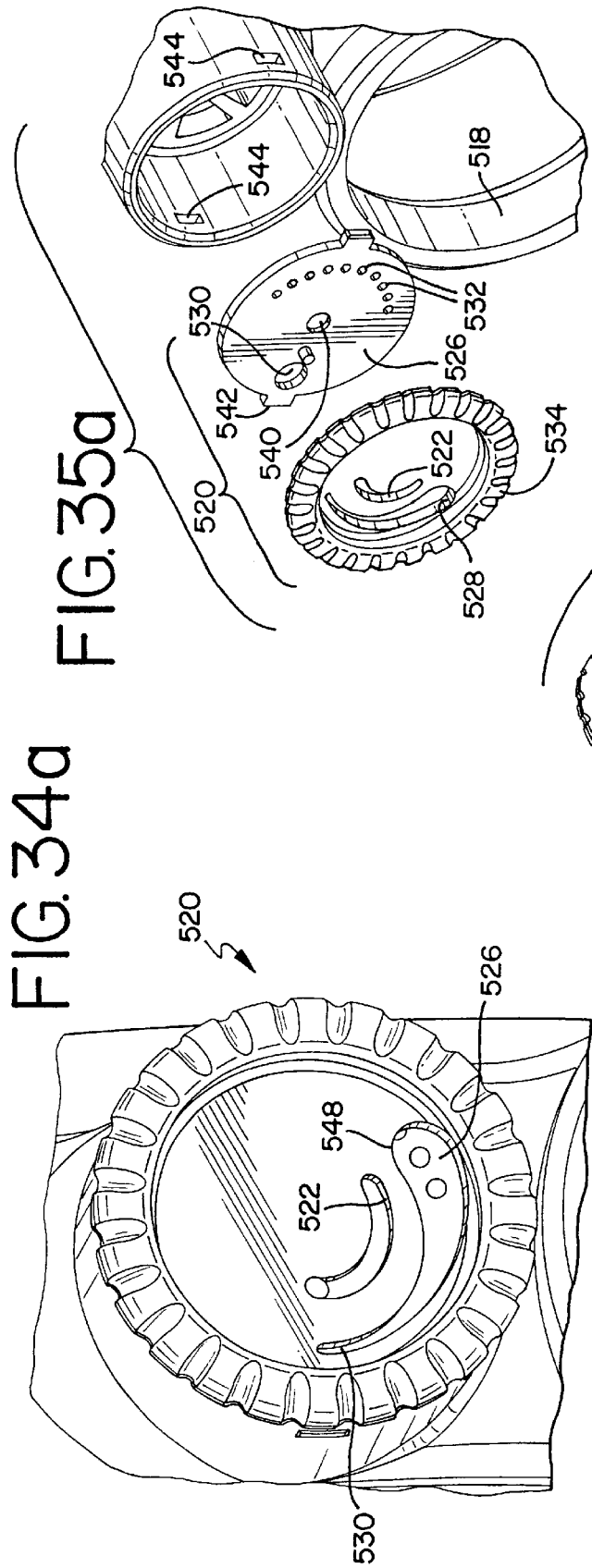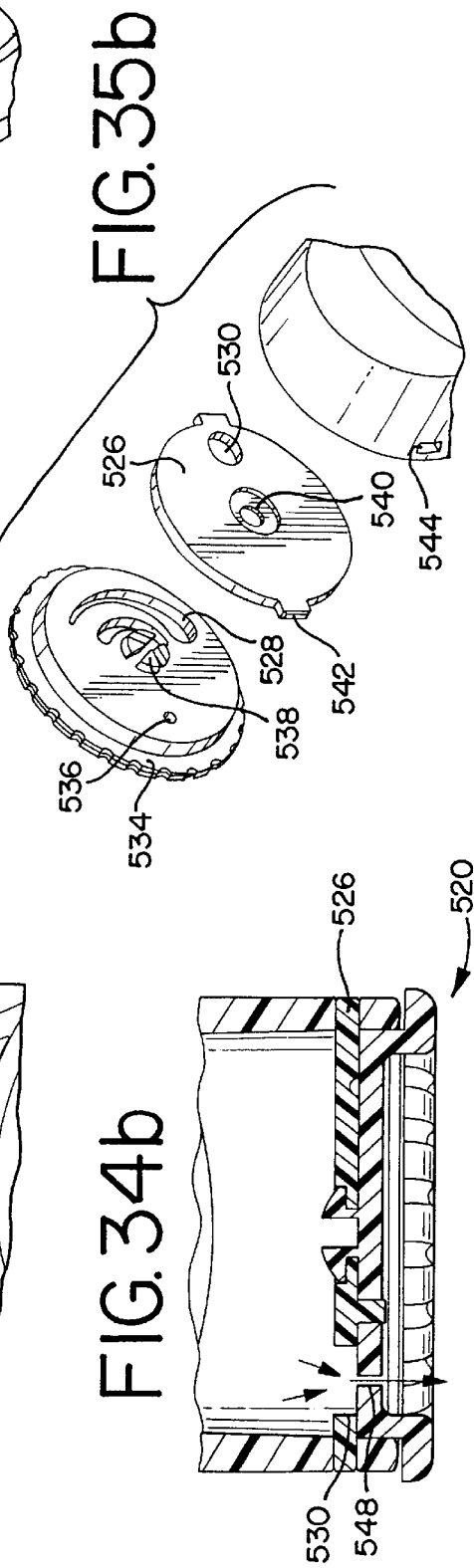

AEROSOL DELIVERY APPARATUS WITH POSITIVE EXPIRATORY PRESSURE CAPACITY

CROSS-REFERENCE TO RELATED APPLICATIONS

This application claims the benefit of U.S. Provisional Application No. 60/196,555, filed Apr. 11, 2000, the entirety of which is incorporated herein by reference.

FIELD OF THE INVENTION

The invention relates to an apparatus and method for performing Positive Expiratory Pressure (PEP) therapy. More particularly, this invention relates to a method and apparatus for performing PEP therapy alone or in conjunction with an aerosol delivery apparatus.

BACKGROUND

PEP therapy is used primarily in pulmonary secretion removal. Devices used to perform PEP therapy provide positive pressure during expiration. The patient or user exhales against a fixed orifice resistor and generates a pressure ranging approximately from 10–20 cm $H_2O$. The resistance orifice is an important consideration and frequently is initially set by a physician, veterinarian, or a skilled practitioner in the art. An orifice that is too large may result in a short exhalation that will not produce proper expiratory pressure. An orifice that is too small may result in a longer expiratory phase that raises the pressure above approximately 20 cm $H_2O$ and ultimately increases the work of breathing.

During the exhalation phase of PEP therapy, the airway is splinted open by the pressure. This causes the movement of secretions from the peripheral airways into the larger airways where they can be expelled. PEP therapy usually lasts for about 10–20 minutes and is performed as required, generally 1–4 times per day. Typically, the patient performs 10–20 PEP breaths, removes the device from their mouth and follows this with a forceful exhalation. This final exhalation triggers a cough that loosens secretions.

Studies indicate that PEP therapy dilates the airways and improves the distribution of ventilation, resulting in a better deposition of an inhaled substance, such as, but not limited to, a medicine or remedy. As used herein, the term "aerosol delivery apparatus" means any apparatus capable of producing and/or delivering a substance, such as, but not limited to, a medicine, in a form suitable for inhalation by a patient and includes, without limitation, an aerosol holding chamber, nebulizer, spacer with integrated actuator, a dry powder inhaler, and a metered dose inhaler.

SUMMARY OF THE INVENTION

One aspect of the present invention is directed to a positive respiratory pressure apparatus including a patient respiratory system interface and a valve assembly in fluid communication with the patient respiratory system interface. The valve assembly has a valve configured to pass a fluid traveling in a predetermined direction from a first side to a second side of the valve, and a variable resistance bypass window positioned adjacent the valve and having a resistance to a fluid traveling in a direction opposed to the predetermined direction, where the variable resistance bypass window is continuously adjustable between a first fluid resistance and a second fluid resistance.

According to another aspect of the invention an apparatus is disclosed that is capable of performing positive expiratory pressure (PEP) therapy alone or in combination with providing a substance, generally in aerosol form. The apparatus includes a positive pressure (PP) valve having a continuously variable respiratory window. As used herein, the term respiratory is intended to encompass both inhalation and exhalation. Whether inhalation resistance or exhalation resistance is called for will be known to one skilled in the art. The valve may be located at or near the output end of an aerosol delivery apparatus. U.S. application Ser. No. 08/938,686 filed Sep. 26, 1997 in the name of Engelbreth et al. and Ser. No. 09/287,997 filed on Apr. 7, 1999 in the name of Schmidt et al. describe exemplary embodiments of an aerosol delivery apparatus and the disclosures of these references are incorporated herein by reference. Further, U.S. Pat. No. 4,470,412 to Nowacki et al., describing a spacer or expansion chamber, is additionally incorporated herein by reference. The aerosol delivery apparatus with the PP apparatus may be used alone or in combination with a mask or mouthpiece.

In one embodiment, the PP apparatus is associated with a mask. The mask with the PP apparatus may be used alone or in combination with an aerosol delivery apparatus. In another embodiment, the PP apparatus is associated with a mouthpiece. The mouthpiece with the PP apparatus may be used alone or in combination with an aerosol delivery apparatus. In a further embodiment, the PP apparatus is associated with a nebulizer. The nebulizer with the PP apparatus may be used alone or in combination with a patient respiratory system interface, such as a mask or mouthpiece. In yet another embodiment, the PP apparatus is associated with a spacer chamber with an integrated actuator. The spacer chamber with the integrated actuator associated with the PP apparatus may be used alone or in combination with a mouthpiece or mask.

In another embodiment, a pressurized metered dose inhaler canister is capable of association with an aerosol holding chamber having a PP valve associated therewith. In yet a further embodiment, a pressurized metered dose inhaler canister is capable of association with an aerosol holding chamber engageable with a mouthpiece or mask having a PP valve associated therewith.

Another aspect of the invention is directed to a kit for performing positive expiratory pressure including an aerosol delivery apparatus, a mouthpiece and/or mask attachable to the output end of the aerosol delivery apparatus, and a PP apparatus. The PP apparatus may be located on the aerosol delivery apparatus or the mouthpiece and/or mask. In alternative embodiments, the PP apparatus may be attached to the aerosol delivery apparatus or integrally formed with the apparatus. The aerosol delivery apparatus, mouthpiece, and PP valve can be combined so as to accomplish positive expiratory therapy and administration of a substance, such as, but not limited to, a medicine in aerosol form. Any aerosol delivery apparatus may be used. In further embodiments of the kit, a backpiece is included for association with an aerosol delivery apparatus. A pressurized metered dose inhaler can engage with the backpiece for delivery of a medicament.

One embodiment of a method of performing positive expiratory pressure therapy includes providing a PP apparatus with a valve that is capable of providing a continuously variable expiratory window. The method further includes performing a series of breaths. When exhalation is performed, the exhalant is directed through the continuously variable expiratory window. Performance of a therapeutic cough triggers the loosening of secretions. Upon loosening of the secretions, a substance, such as a medicament, may be provided for inhalation into the respiratory system. In an alternative embodiment of method, the PP valve may be positioned so as to provide positive inspiratory pressure upon inhalation into the apparatus.

A further aspect of another embodiment includes association of a PP apparatus associable with a mask or mouthpiece engageable with a backpiece device. The backpiece device includes a plastic or an elastomeric adapter suited to receive the mouthpiece of a pressurized metered dose inhaler.

One embodiment of a method of performing positive expiratory pressure therapy includes providing a positive expiratory pressure apparatus having a valve capable of providing a continuously variable resistance window, performing a series of breaths including inhalation and exhalation; exhaling so that the exhalant is directed through the continuously variable resistance window, performing a therapeutic cough triggering the loosening of secretions, and providing an inhaleable medicament.

Another embodiment of a method of performing positive expiratory pressure therapy includes providing a positive respiratory pressure apparatus having a valve capable of providing a continuously adjustable resistance to exhalation, where the valve is located in a mouthpiece attachable to a chamber. A patient then executes a series of therapeutic breaths, including inhalation and exhalation, wherein the exhalant is directed through the continuously adjustable resistance window, the patient performs a therapeutic cough triggering the loosening of secretions, and medicament is provided via the chamber.

According to another aspect of the invention, a method of performing positive expiratory pressure therapy in combination with providing an aerosolized medicament includes providing a positive expiratory pressure apparatus having a positive expiratory pressure valve capable of providing a continuously variable resistance window, where the valve is positionable in a mouthpiece and the mouthpiece attachable to an aerosol holding chamber. A series of therapeutic breaths, including inhalation and exhalation, are then taken where the exhalant is directed through the continuously variable resistance window. The continuously variable resistance window is preferably capable of providing a variable back pressure to the exhalant. A therapeutic cough capable of triggering the loosening of sections is performed and aerosolized medicament from the aerosol holding chamber is administered through inhalation.

One embodiment of an apparatus capable of performing positive respiratory pressure therapy in combination with providing an aerosolized medicament includes a positive respiratory pressure valve having a continuously variable resistance window; and an aerosol holding chamber having an output end, the positive respiratory pressure valve locatable at the output end.

Another embodiment of an apparatus capable of performing positive respiratory pressure therapy includes a positive respiratory pressure valve having a slide control, the slide control providing a continuously variable resistance window; and a mouthpiece, the mouthpiece having a first and a second end, the second end capable of association with the positive respiratory pressure valve.

Yet another embodiment of an apparatus capable of performing positive respiratory pressure therapy in combination with providing an aerosolized medicament includes a positive respiratory pressure valve having a continuously variable resistance window; an aerosol holding chamber having an input end and an output end, the positive respiratory pressure valve locatable at the output end; and a metered dose inhaler canister capable of association with the input end of the aerosol holding chamber.

A still further embodiment of a kit for performing positive expiratory pressure includes an aerosol holding chamber having an inlet and an outlet. A backpiece is attachable to the inlet of the aerosol holding chamber with a metered dose inhaler capable of association with the backpiece. A mouthpiece is attachable to the outlet of the aerosol holding chamber. A positive expiratory pressure valve is generally locatable at the outlet end of the aerosol holding chamber, wherein the aerosol holding chamber, backpiece, mouthpiece, and positive expiratory pressure valve can be combined so as to accomplish positive expiratory therapy and administration of an aerosolized medicament.

An additional embodiment of an apparatus capable of performing positive expiratory pressure therapy in combination with providing an aerosolized medicament includes a positive expiratory pressure valve having a continuously variable resistance window, a mouthpiece, the positive expiratory pressure valve associable with the mouthpiece, and a nebulizer having an input end and an output end, the positive expiratory pressure valve associable with the output end.

Further embodiments include a mouthpiece wherein the improvement comprises a positive pressure valve. An additional embodiment includes a nebulizer wherein the improvement comprises a positive pressure valve. Moreover, an embodiment includes an aerosol holding chamber wherein the improvement comprises a positive pressure valve. A yet further embodiment includes a pressurized metered dose inhaler wherein the improvement comprises a positive pressure valve.

The invention will best be understood by reference to the following detailed description of the preferred embodiment, taken in conjunction with the accompanying drawings. The discussion below is descriptive, illustrative and exemplary and is not to be taken as limiting the scope defined by any appended claims.

BRIEF DESCRIPTION OF SEVERAL VIEWS OF THE DRAWINGS

FIG. 1 is a cross sectional view of a mouthpiece associable with a chamber in conjunction with a PP apparatus.

FIG. 2 is a perspective view of a mouthpiece associable with a chamber in conjunction with the PP apparatus.

FIG. 3 is an exploded view of the preferred embodiment.

FIG. 4a is a front view of one embodiment of the PP apparatus.

FIG. 4b is a cross section drawn along line A—A of FIG. 4a.

FIG. 4c is a back view of one embodiment of the PP apparatus.

FIG. 4d is a cross section drawn along line B—B of FIG. 4a.

FIG. 4e is a sectional cross section drawn along line C—C of FIG. 4a.

FIG. 4f is a rear perspective view of the embodiment of FIG. 4a.

FIG. 8d is a cross section drawn along line A—A of FIG. 8a.

FIG. 12 is one embodiment of the slide control having a port.

FIG. 13 is one embodiment of the mouthpiece showing the annular sealing ring.

FIG. 14 is one embodiment showing a plurality of detent notches.

FIG. 20 is a perspective view of a duck-bill valve used in the PP apparatus of FIGS. 18–19.

FIG. 21 is a cross-sectional view of the duck-bill valve of FIG. 20.

FIG. 22a is a front exploded view of one embodiment of the PP apparatus in conjunction with a mouthpiece and associable with a spacer.

FIG. 22b is a rear exploded view of one embodiment of the PP apparatus in conjunction with a mouthpiece and associable with a spacer.

FIG. 22c is a front view of one embodiment of a valve showing the baffle.

FIG. 30 is an exploded view of a PP apparatus associated with a mouthpiece and having an exhalation valve.

FIG. 31 is a further perspective view of one embodiment of the PP apparatus in conjunction with a mask having an opening for association with a chamber.

FIG. 34a is a close up of one embodiment of the PP apparatus having a plurality of variable sized flow ports, in conjunction with a mask.

FIG. 34b is a cross section of one embodiment of the PP apparatus having a plurality of variable sized flow ports, in conjunction with a mask.

FIG. 35a is a front exploded view of a close up of one embodiment of the PP apparatus having a plurality of variable sized flow ports, in conjunction with a mask.

FIG. 35b is a rear exploded view of a close up of one embodiment of the PP apparatus having a plurality of variable sized flow ports, in conjunction with a mask.

DETAILED DESCRIPTION OF THE PRESENTLY PREFERRED EMBODIMENTS

Figure 5:
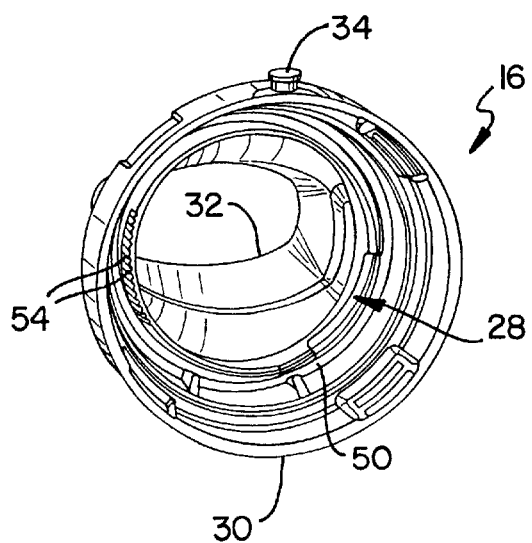
FIG. 5 is a rear perspective of a mouthpiece according to a preferred embodiment.

FIGS. 1–3 show one embodiment of an assembly 10 for performing positive expiratory pressure (PEP) therapy where the assembly incorporates a positive pressure (PP) device having a PP valve 12. The assembly 10 includes an aerosol delivery apparatus, such as an aerosol holding chamber 14, and a patient respiratory system interface, such as a mouthpiece 16 and/or mask attachable to the output end of the aerosol delivery apparatus. The PP valve 12 may be located on the aerosol delivery apparatus or the patient respiratory system interface. The assembly 10 combines the aerosol delivery apparatus, mouthpiece, and PP valve into a tool for use in both positive expiratory therapy and administration of a substance, such as a medicament, in aerosol form. Any aerosol delivery apparatus suitable for generating an aerosol of the desired substance may be used.

In the embodiment of FIGS. 1–3, a backpiece 18 is attachable to the inlet 20 of the aerosol holding chamber 14. A metered dose inhaler (not shown) may be connected with the backpiece 18. The mouthpiece 16 is attachable to the outlet end 22 of the aerosol holding chamber 72. The PP valve 12 is generally locatable at the outlet end 22 of the aerosol holding chamber 14. FIG. 3 depicts an exploded view of the PEP assembly showing an annular valve 24 positioned between the outlet end 22 and the mouthpiece 16. More details on the aerosol holding chamber 14 disclosed in FIGS. 1–3 may be found in U.S. Pat. No. 4,470,412 and U.S. patent application Ser. No. 09/287,997 incorporated above.

In the embodiment depicted in FIGS. 1 and 2, the aerosol holding chamber 14 is provided with an annular valve 24 located at its outlet end 22. The annular valve 24 allows the user to inhale medicament from the chamber 14, but prevents exhalation back through the chamber. As illustrated in FIGS. 1–3, and in more detail in FIGS. 4a–4f, 5 and 7, a PP valve 12 may be formed in a mouthpiece 16. The PP valve 12 includes a slide control 26 that is movably positioned relative to a resistance window 28. The slide control 26 is variably maneuverable to cover or uncover the resistance window 28 in a continuous manner. Further, the movement of the slide control 26 includes, but is not limited to, covering or uncovering, and/or opening or closing, the resistance window 28 or any variations thereof.

The PP valve 12 may be located on or in conjunction with a mouthpiece 16. An exemplary embodiment of the mouthpiece 16 shown in FIGS. 4a–4f has a distal end 30 and a proximal end 32. Commonly, the proximal end 32 of the mouthpiece is inserted or associated with the mouth or nostrils of the user. Additionally, the distal end 30 of a mouthpiece may or may not be associated with an aerosol delivery apparatus and the mouthpiece alone may be configured to constitute a PEP device.

Generally, in one exemplary embodiment, the PP valve 12 may be located at or near the distal end 30 of the mouthpiece 16. Although, it is understood that the PP valve 14 may be located anywhere on the mouthpiece 1 and its location is not to be limited. In an alternative embodiment, the PP valve 12 may be located at or near the output end 20 of the aerosol delivery apparatus, such as, but not limited to, the aerosol holding chamber 14 of FIGS. 1–3. Generally, the direction of travel of any fluid, particularly an aerosol or nebulizer medicament, is in the direction from the input end 20, through the channel or chamber body, and to or out the output end 22. This direction of travel from input end 20 to output end 22 is referred to as travel from downstream to upstream.

In a preferred embodiment the mouthpiece 16 is formed of plastic. The plastic may be either rigid or soft. Other materials that can also be used for the mouthpiece 16 include metal or other materials known to one in the art. In the embodiment depicted in FIGS. 1–3, 4a, 4b, 4c, and 4f, a tab 34 is provided allowing for the connection of a cap 36, as shown in FIG. 2, to cover the proximal end 32 of the mouthpiece 16. In a preferred embodiment, the mouthpiece 16 may include indicia 35, or setting indications, representing the resistance setting. The indicia 35 may be in the form of numbers, bars, colors, a series of dots or the like.

Figure 7A:
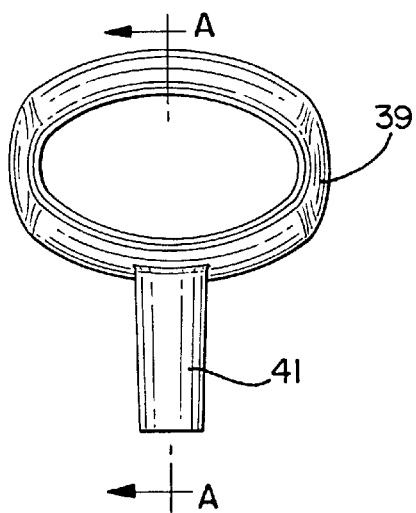
FIG. 7a is a front view of the fitting and manometer port.
Figure 7B:
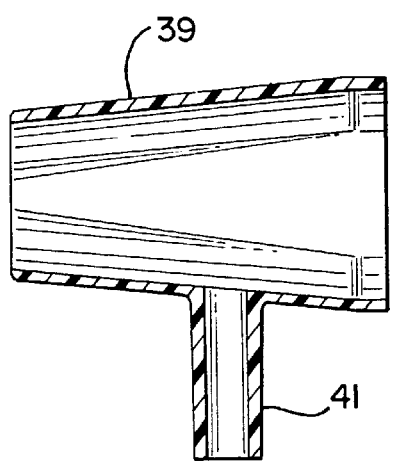
FIG. 7b is a cross section drawn along line A—A of FIG. 7a of the fitting and port.

In a further embodiment, as shown in FIGS. 7a and 7b, the PP apparatus 10 may includes a fitting 39 sized for placement over the proximal end of the mouthpiece. The fitting 39 includes a manometer port 41 extending from the fitting over which a manometer can be attached. In a preferred embodiment the fitting 39 is formed of a plastic. The plastic may be either rigid or soft. Other materials that can also be used to form the fitting include metal.

Figure 8A:
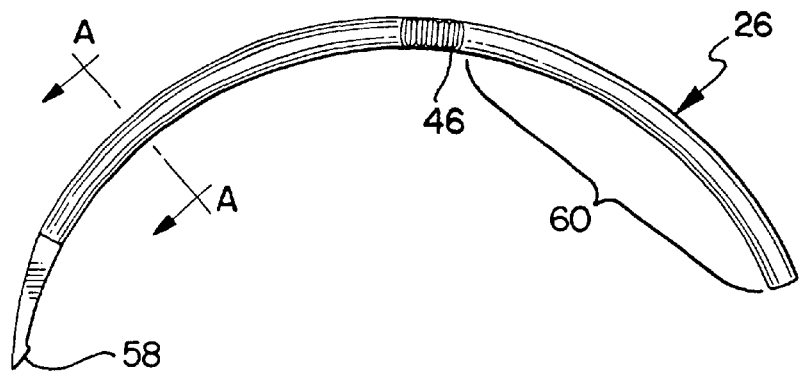
FIG. 8a is a top view of one embodiment of the slide control.
Figure 8B:
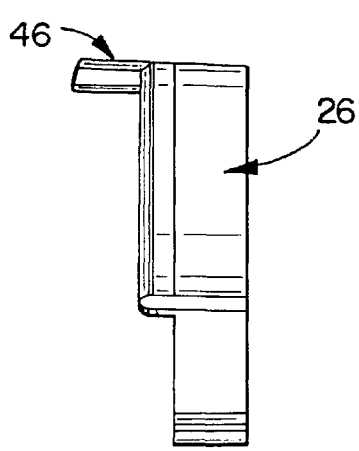
FIG. 8b is a side view of one embodiment of the slide control.
Figure 8C:
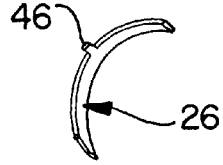
FIG. 8c is a perspective view of one embodiment of the slide control.
Figure 8D:
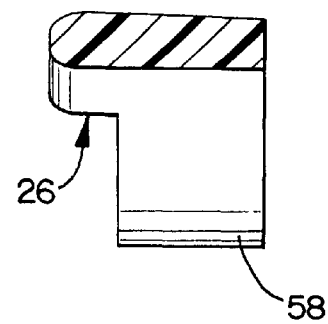
Figure 9:
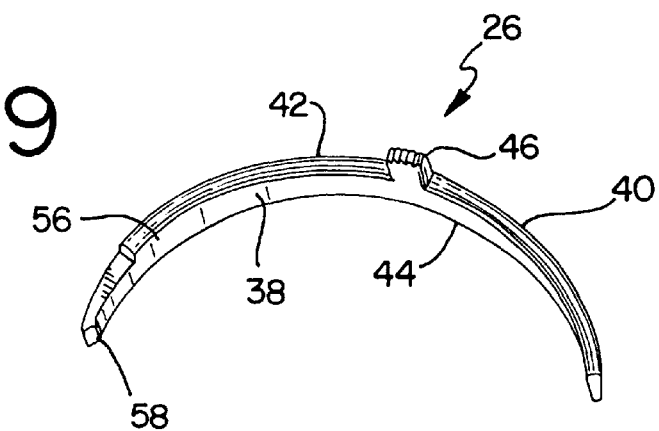
FIG. 9 is a top perspective view of one embodiment of the slide control.

FIGS. 3, 8a–8d and 9 show an embodiment of the slide control 26 of the PP apparatus 10. As shown in FIG. 9, in the illustrated embodiment, the slide control 26 is of a semi-circular, quarter moon shape. The slide control 26 has a first lateral side 38 concave in shape and a second lateral side 40 opposite the first side 38. The slide control 26 also has a top 42 and a bottom 44 surface. From the top surface 42 of the slide control 26 extends a tab setting 46.

In the illustrated embodiment, the tab setting 46 is a uniformly molded projection from the slide control 26. In a preferred embodiment, the tab setting 46 has smooth edges for easy engagement with the finger, thumb or appendix of the user. The tab setting 46 may also have a serrated edge or any other edge known in the art. When assembled with the mouthpiece 16, the tab setting 46 projects through the mouthpiece from the tab window 48. The user of the device manipulates the tab setting 46 in such a manner as to cause, either directly or indirectly, the movement of the slide control 26 thereby varying the opening of the resistance window 28.

In the embodiment of FIGS. 1–3, 4a–4f, 5 and 7, the tab window 48 is arcuate in shape, parallel to the contour of the circumference of the mouthpiece 16. Referring to FIG. 4f, the slide control 26 is preferably seated in a channel 50 located on the mouthpiece 16. The slide control 26 is held within the channel 50 by at least one tooth 52. Located on one or both of the walls of the channel 50 is a stepped surface 54 as shown in FIG. 5.

Figure 6:
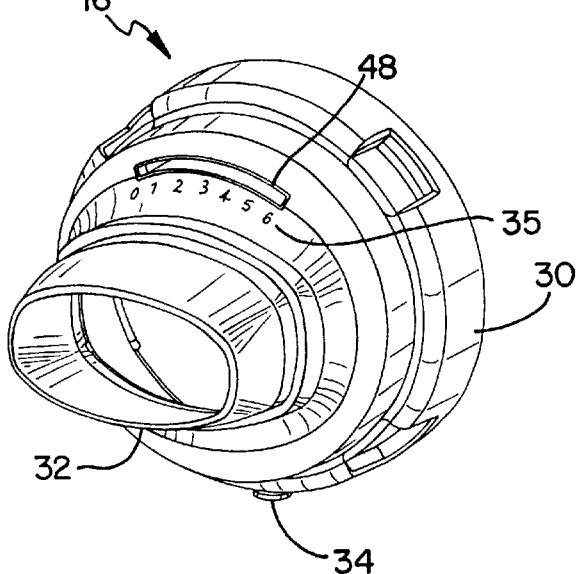
FIG. 6 is a front perspective view of a mouthpiece with one embodiment of the PP apparatus.

In the embodiment shown in FIGS. 8a and 6, the control arm 56 of the slide control 26 is shown having a finger protection 58 from one end of the slide control 26. In another embodiment, the slide control 26 may have a control arm 56 located on both ends of the slide control 26. The finger projection 58 is capable of engagement with the stepped surface 54 inside the mouthpiece shown in FIGS. 4c and 5. In the illustrated embodiment, the stepped surface 54 includes a series of ribs extending a variable length of the internal diameter of the mouthpiece 16. In another embodiment, as shown in FIG. 30, the stepped surface 54 may also be located along the tab window 48. Therefore, the location of the stepped surface 54 may vary while remaining engageable by the control arm 56. Additionally, the stepped surface 54 may be located on either or both of the internal walls of the channel 46. In the embodiment of FIGS. 4a–4f and 8a–8d, the slide control 26 is of a flexible material so that the control arm 56 can slide across the uppermost surface of the ribs projecting from the stepped surface 54. When the desired opening of the resistance window 28 is obtained, the control arm 56 engages in a semi-locked manner the ribs projecting from the stepped surface 54.

The end of the slide control 26 opposite the control arm 56 may either be provided with a finger projection 58 or may be smooth. The length of the slide control 26 extending from the tab setting 46 to the end of the control arm 56 opposite the projection 58 is generally the length of the resistance window 28. This resistance control length 60 is at least the length that the resistance window 28 can be opened allowing for exhalant to exit the window 28. In a preferred embodiment, the slide control 26 is manufactured of a plastic. The plastic may be either rigid or soft. Other materials that can also be used for the slide control 26 include metal or other materials known in the art.

In general, as shown in FIG. 5, the resistance window 28 may be an opening of any size or shape in the walls defining the channel 46 in the mouthpiece 16 which, in conjunction with the illustrated embodiment of the slide control 26, provides an opening in the mouthpiece 16 to produce sufficient pressure during exhalation of the patient performing PEP therapy. For example, the resistance window 28 may be formed with straight or slanted edges. If the edges are slanted, this provides a steeped effect to the resistance window 28. If the desired exhalation pressure is determined to range from 10–20 cm H₂O, then the resistance window 28 in conjunction with the slide control 26, acting as a cover or closure mechanism for the resistance window 28, are sized in such a manner as to provide an appropriate opening for the desired exhalation pressure to be produced. As one example, if the resistance window 28 is generally narrow, then the length of the window may be of a longer length so as to provide a large enough opening through which PEP therapy is performed. Interdependent in the relationship is the resistance window length 60 of the control arm 26. In the above example, the resistance window length 60 of the control arm 26 is generally longer to cover the desired amount of the resistance window 28. The control arm 26 may provide a continuously adjustable variable resistance window between a first position where the control arm completely blocks the window 28, to a second position where the control arm leaves the window completely open.

Figure 15:
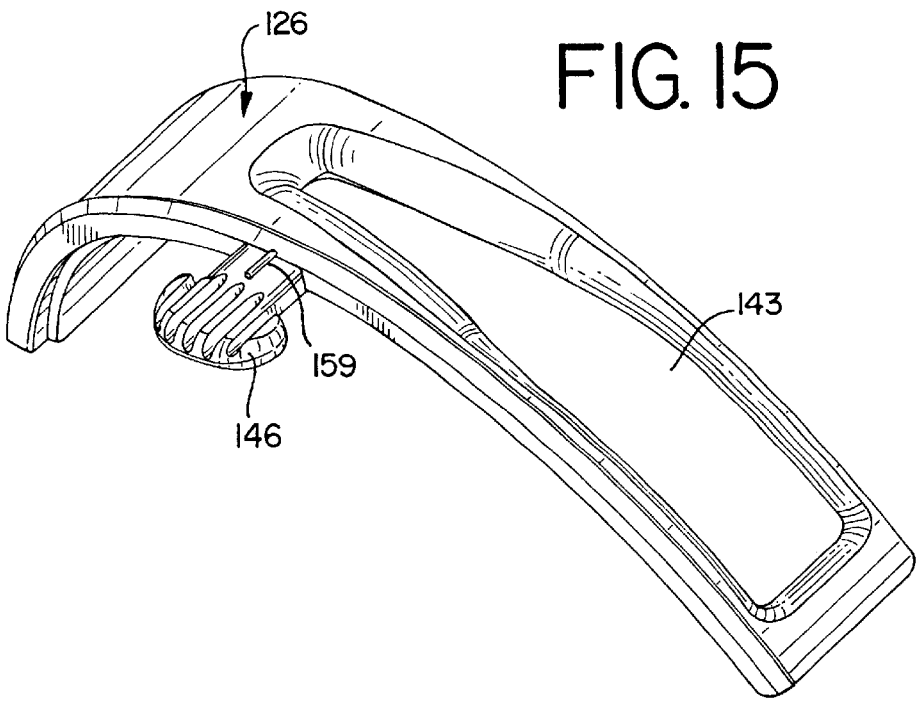
FIG. 15 is a side view of one embodiment of the control valve showing the port.

An alternative embodiment of an assembly 100 for performing PEP therapy is shown in FIGS. 10–17. This embodiment is similar to the embodiment of FIGS. 11–13, but utilizes a variation of the resistance window and slide control in the PP valve 112. In the assembly 100 of FIGS. 10–17, the resistance window 128 and slide control 126 are positioned in the mouthpiece 116. The tab setting 146 of the slide control 126 is of a flexible material. A detent 158 protrudes from the first tab setting face 156 located on the concave side 125 of the slide control 126. As shown in FIG. 15, a position indicating rib 159 is located on the tab setting 146 opposite the detent 158. In the illustrated embodiment, the rib 159 is shown as a generally rectangular protrusion from the surface of the tab setting 146. Yet, the rib 159 may be any shape protrusion, such as but not limited to circular, triangular. Further, the rib 159 may not be a protrusion at all but rather is a concave marking on the surface of the tab setting 146. The rib 159 has at least the function of indicating to the user the extent of the opening of the resistance window 128. Therefore, one skilled in the art can envision a variety of marking, shapes, indents or protrusions, or colors which serve at least the function of indicating the extent of the opening of the resistance window 28.

Figure 10:
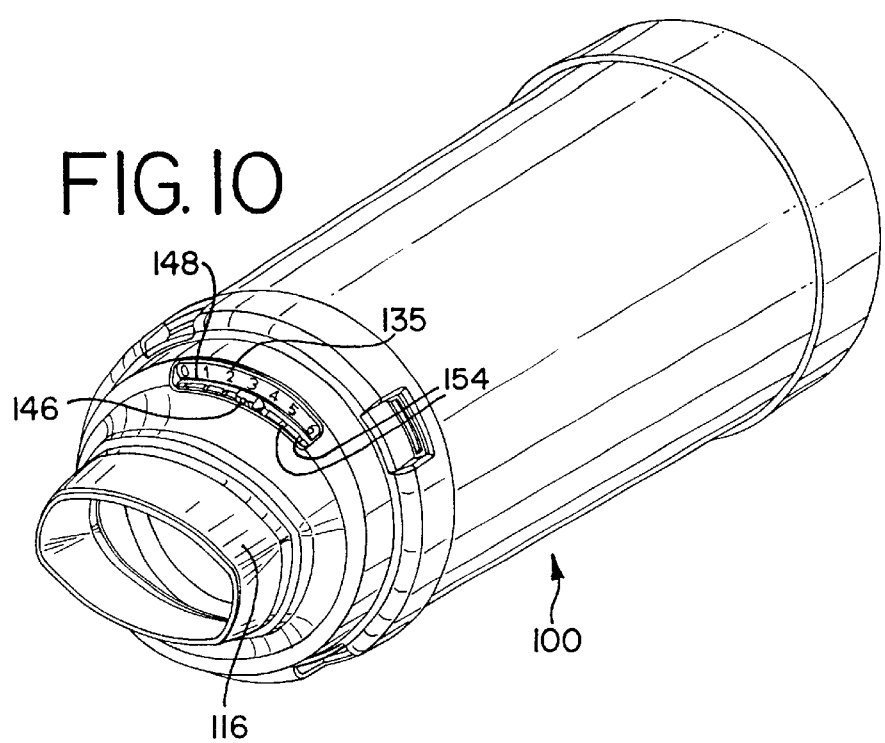
FIG. 10 is a perspective view of an alternative embodiment of the PP apparatus of FIGS. 1–3 showing detent notches in conjunction with a mouthpiece.
Figure 11:
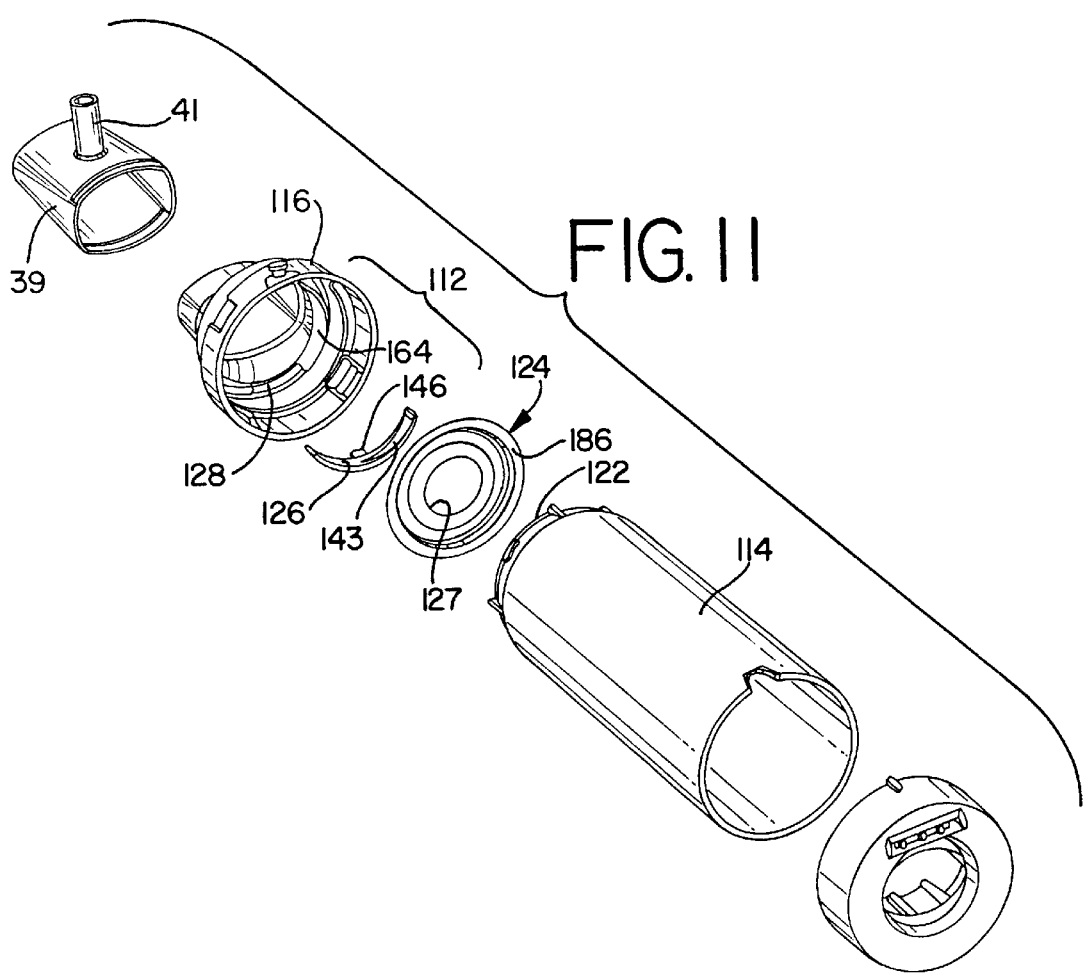
FIG. 11 is an exploded view of one embodiment showing a slide control having a port.

The detent 158 located on the tab setting 146 is associated with at least one detent notch 154 as shown in FIGS. 10 and 14. The flexible tab setting 146 is movable within the tab window 148. The one or more detent notches 154 are preferably located along the boundary of the tab window 148 and indicia 135, representative of exhalation effort corresponding to the position of the slide control 126, are arranged adjacent the respective detent positions. FIGS. 10 and 14 show a plurality of detent notches 154. In operation, the flexible tab setting 146 is moved along the tab window 148. The detent 154 located on the first tab fitting face 125 of the tab setting 146 moves into and out of engagement with the detent notches 154. Movement along the boundary and engagement with the detent notches 154 removably fixes the slide control 126 in a variety of positions. Each varied position provides for a further opening or closing of the resistance window 128. Further, in operation, the detent 158 is not limited to being engaged with a detent notch but may be engaged or seated at any point along the boundary. Engagement with, or seating within, a detent notch 154 of a detent 158 provides for a variable securely fixed opening of the resistance window 128. Each detent notch 154 may correspond to a particular size opening or pre-set opening of the resistance window 128. Therefore, by engagement of the detent 158 within the detent notch 154, the user may be provided with a pre-set resistance window opening 128. Yet, the detent notch 154 may also be positioned anywhere along the boundary providing for a continuously variable resistance window opening 128.

Figure 16:
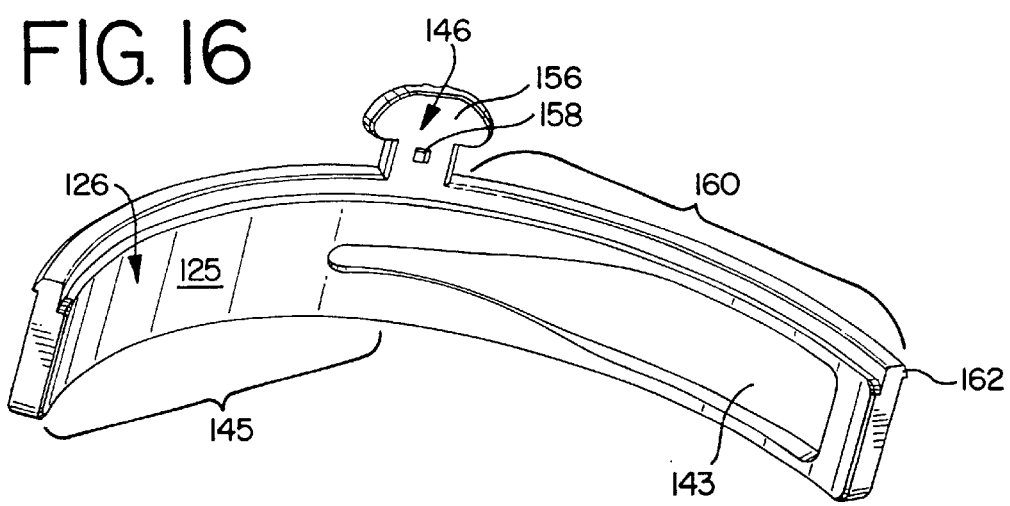
FIG. 16 is a concave perspective view of the slide control showing the port.
Figure 17:
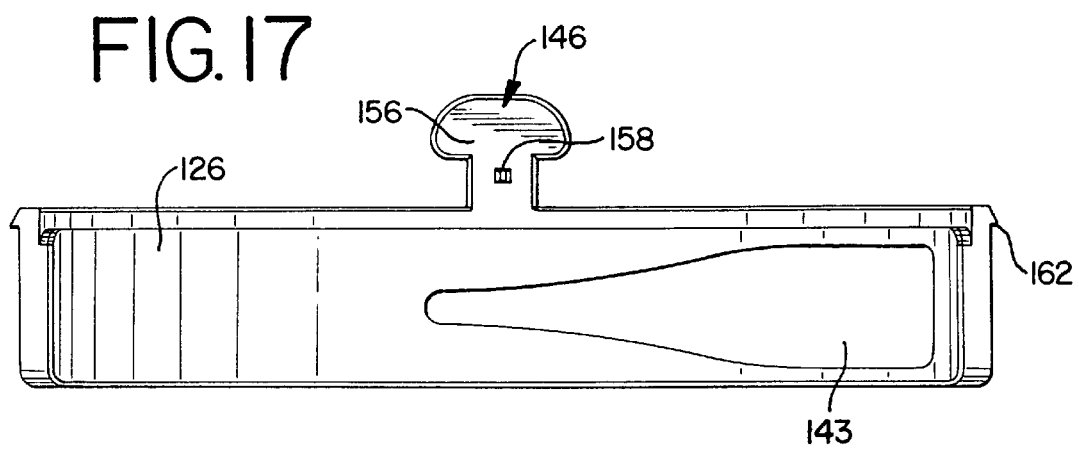
FIG. 17 is a concave bottom view of the slide control showing the port.

The slide control 126, as shown in FIGS. 15,16 and 17 has located therein a port 143. The port 143 may be of any size or shape and in the illustrated embodiment is generally a rounded triangle having an elongated point. The port 143 operates in conjunction with the resistance window 128. In the embodiment illustrated in FIGS. 10–17, the size of the opening through which the exhalant passes is determined by how much of the port 143 is left uncovered or open and aligned with the resistance window 128. The slide control 126 is provided with a closure area 145, as shown in FIG. 16. Further, the slide control 126 is provided additionally with a port area 160. When the resistance window 128 is closed or not open and thereby not allowing for the exiting of any exhalant, the closure area 145 of the slide control 126 is congruent with or aligned with the resistance window 128. As the slide control 126 is gradually moved, the port area 160 containing the port 143 is brought into alignment with the resistance window 128 in the mouthpiece 116. In this manner, a continuously variable opening is provided. For example, as the slide control 126 moves aligning a greater and greater amount of the port 143 with the resistance window 128, a greater opening or path for the exhalant is provided.

As described above, and similar to the embodiment of FIGS. 1–3, the slide control 126 is seated in a channel 150 located on the mouthpiece 116. The slide control 126 is slidably movable within the channel 150 in the manner described above so as to continuously variably align the port 160 with the resistance window 128. In the embodiment of the slide control 126 illustrated in FIGS. 13, 16, and 17, a retaining ridge 162 fits into the channel 150 thereby holding the slide control 126 in its desired position throughout its range of motion in the mouthpiece. The desired position of the slide control 126 is as close as possible to the annular sealing ring 164 shown in FIG. 13. One function of the annular sealing ring 164 is to prevent leakage of the exhalant to ensure that the exhalant to the greatest extent exits from the resistance window 128. In a further embodiment, the PP valve 112 may optionally be provided with at least one locating ring or post 166 to help maintain the slide control 126 in alignment. As with the embodiment of FIGS. 1–3, a patient's exhalation effort is controlled by adjusting the slide control over the resistance window so that the patient's exhaled air, which is prevented from entering the aerosol chamber 114 by the annular valve 124 and a baffle (not shown), must exit through the resistance window and provide a desired exhalation resistance. More specifically, during inhalation the inner diameter 127 of the annular valve 124 (FIG. 11) unseats from the baffle (not shown) on the output end 122 of the aerosol holding chamber and permits passage of fluid. Substantially simultaneously, the exhalation flange 186 of the valve 124 flexes to seal against the outer ridge 188 (FIG. 13) formed inside the mouthpiece 116 to prevent ambient air from entering the mouthpiece. During exhalation, the process is reversed and the inner diameter 127 prevents exhalant from entering the aerosol holding chamber while the exhalation flange 186 flexes away from the outer ridge 188. Thus, the exhalant preferably passes through the resistance window 128 and may escape to the outside between the exhalation flange and the mouthpiece, and then through the gap between the mouthpiece and aerosol holding chamber.

Referring to FIGS. 18–21, an alternative embodiment of an assembly 210 for PEP therapy combined with an aerosol delivery apparatus is shown. The aerosol delivery apparatus includes a chamber housing 214 having an input end 220 and an output end 222. The chamber housing 214, input end 220, and output end 222 define an interior space 223. The apparatus may also include an elastomeric backpiece which may be similar to the backpiece in the embodiment shown in FIGS. 1–3. The output end 222 of the chamber housing 214 is shaped to receive the mouthpiece 216 and includes locking tabs 281 and a protrusion 283. The protrusion 283 is preferably annular in shape. The locking tabs 281 are spaced apart around the outside of the output end 222.

Figure 18:
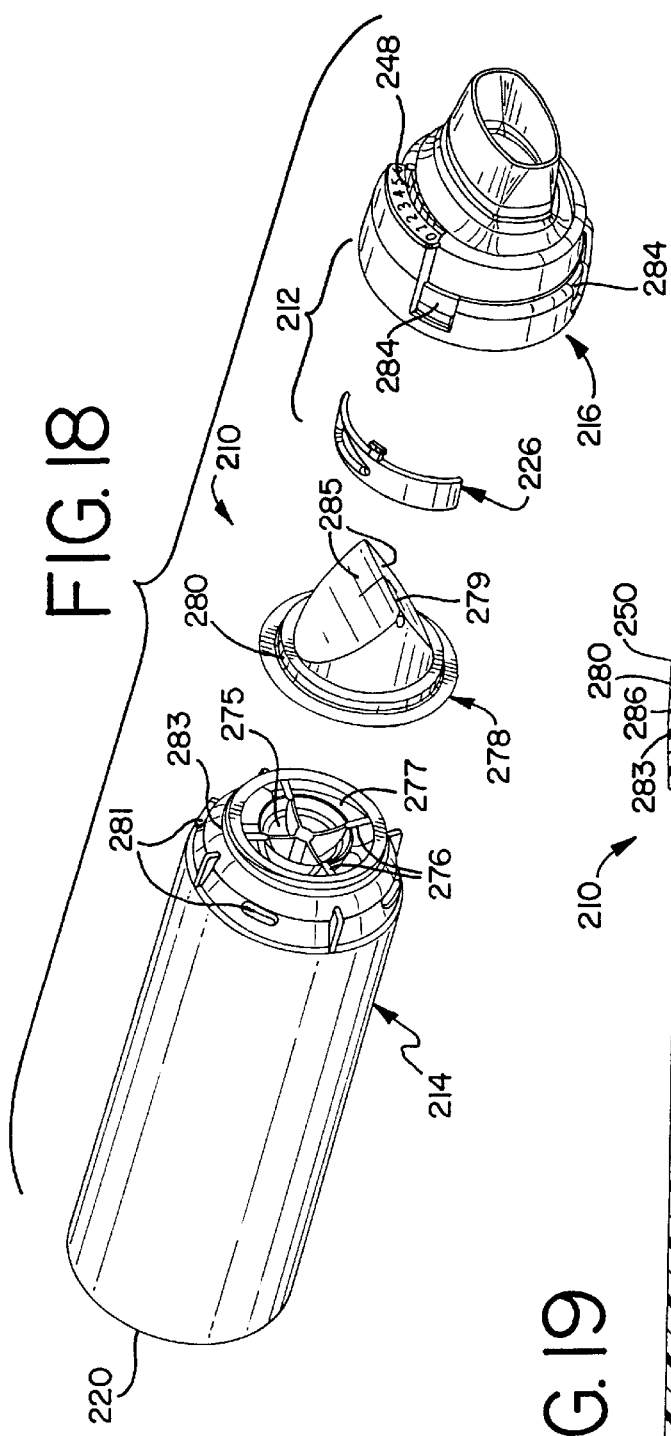
FIG. 18 is an exploded view of an alternative embodiment of the PP apparatus of FIGS. 8–10.
Figure 19:
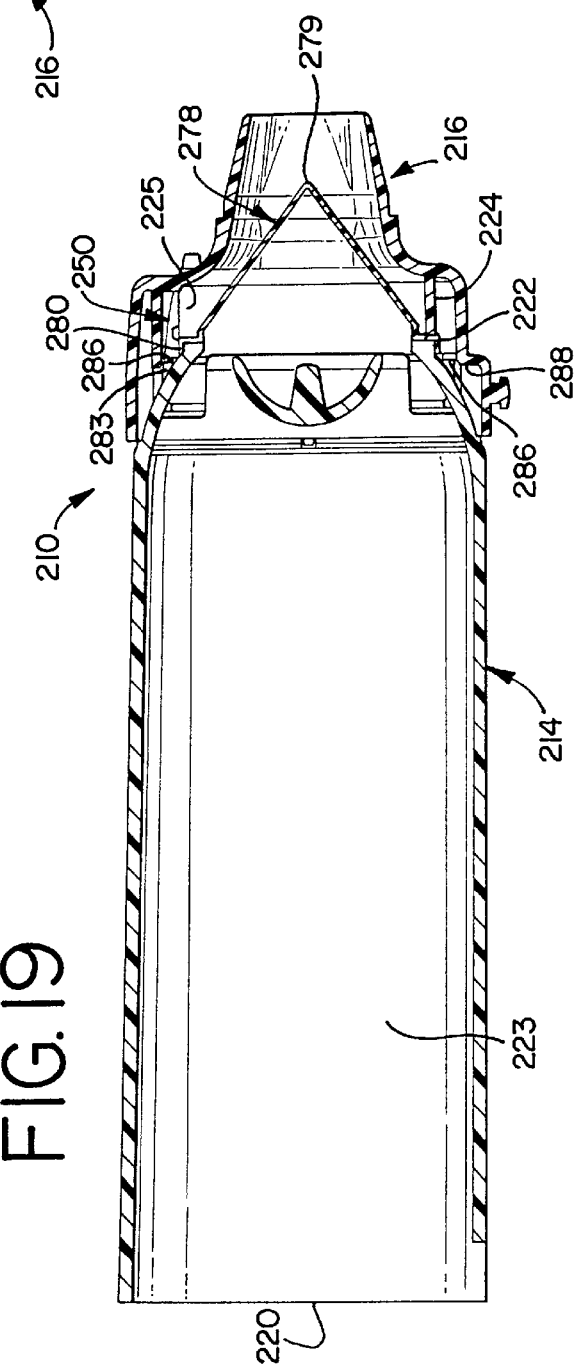
FIG. 19 is a cross-sectional view of the PP apparatus of FIG. 18.

Referring to FIGS. 18–19, the mouthpiece assembly 216 is preferably substantially similar to that illustrated in FIGS. 10–15. The mouthpiece assembly includes an annular sealing ring 224, and a resistance window defined by a gap 225 in the sealing ring. A slide control 226 is slidably seated in a channel 250 between the annular sealing ring and support posts or a support ring. The tab setting 246 protrudes from the tab window 248 in the mouthpiece 216. The continuously variable resistance function is achieved as described above, using either embodiment of slide control and nozzle described above.

The mouthpiece assembly 216 is connected to the output end 222 of the chamber housing 214 by placing the apertures 284 over the locking tabs 281. As with the embodiment of FIGS. 1–3 and 10–17, in the embodiment of FIGS. 18–21 a containment baffle 275 may be integrally formed with the chamber housing 214 from a single piece of material and located near the outlet end 222. As shown in FIG. 18, the containment baffle 275 includes connecting members 276 that extend from the edge of the containment baffle to the inner diameter of the output end 222 in the chamber housing. Vents 277 are defined between the outer perimeter of the containment baffle and the inner diameter of the outlet end of the chamber housing and are separated by the connecting members. The vents 277 are arcuate in shape and conform to the outer perimeter of the containment baffle 275. In a preferred embodiment, the containment baffle is dome-shaped where the concave end points towards the chamber 223. In alternative embodiments, the containment baffle may be any of a number of geometric shapes.

A valve 278 having a valve member 279 and a valve seat 280 is shown. The valve seat 280 preferably comprises the rim of the valve and the corresponding raised lip 283 on the outlet end 222 of the chamber housing 214. The valve member has a sealing surface that preferably forms between two parallel portions, or lips, of the valve. In a preferred embodiment, the valve material seals against itself when fluid flows against a predetermined flow direction of the valve. In the embodiment shown, the valve is a duck-bill valve where the valve seat 280 is positioned axially away from the valve opening. The valve 278 defines a central open area toward the end having the valve seat. The valve member 279, shown as parallel sealing lips in FIGS. 18–21, acts to allow passage of fluid on inhalation, but upon exhalation, the lips of the valve member are held together by the force of fluid (e.g. exhaled air) pressing against the walls 285 of the valve member and collapsing the lips of the valve member 279 against each other in a closed position. The valve seat 280 also provides a seal against the chamber housing 214 during exhalation so that exhalant from a patient must be directed through the continuously variable resistance window in the mouthpiece.

In one preferred embodiment, the duck-bill valve 278 has a central open area 274 at its base that has a diameter of approximately 26.09 millimeters (mm). The width of the lips that form the valve member 279 is approximately 21.35 mm and the angle at which the walls 285 converge is approximately 72 degrees. Also, the height of the duck-bill valve 278 measured from the upper portion 282 of the valve seat to the valve member 279 is approximately 18.8 mm. The mouthpiece 216 for containing this valve 278 preferably includes a resistance widow gap 225 having a length of 59 degrees of arcuate cut in the annular sealing ring 224, where the annular sealing ring is approximately 31.4 mm in diameter and has a height of 4.5 mm.

The operation of the apparatus will now be discussed generally with reference to the embodiments of FIGS. 1–3, 10–17 and 18–21. At rest, the valve is adjacent to the output end of the chamber housing. In the annular valve embodiment of FIGS. 1–3 and 10–17 the inner portion of the valve covers the vents at the outlet end of the chamber housing. In the duck-bill embodiment of FIGS. 18–21, the entire outlet end is covered by the valve. For either valve embodiment, the mouthpiece and outlet end of the chamber housing traps the valve in place. Inhalation by the patient causes the sealing portion of the annular valve to move, or alternatively the lips of the duck-bill valve to separate, and permit fluid to pass. Fluid from the chamber housing may be inhaled into the patient's respiratory system through the mouthpiece. The patient may then exhale into the mouthpiece.

Exhalation by the patient results in air traveling through the mouthpiece in a direction opposite the predetermined inhalation flow path of the valve. This air, which is blocked from passage through the valve along the inhalation path, then passes along a second path through the resistance window in the mouthpiece. Also, the force of the exhaled air causes the outer portion of the valve to move away from the mouthpiece in a direction towards the chamber housing. As a result, an exhalation pathway is created between the outer portion of the valve and the mouthpiece through which the exhaled air passes out to the atmosphere or some other predetermined location. As described above, the amount of effort that exhalation requires is set by the slide control, which may be set to block the appropriate amount of the resistance window to achieve the desired resistance.

Referring specifically to the duck-bill valve embodiment of FIGS. 18–21, the duck-bill valve 278 assists both in preventing inhalation of ambient air through the resistance window 225 and providing an exhalation path for exhalant. When the apparatus 210 is assembled (FIG. 19), the upper portion 282 of the valve seat seals against the annular sealing ring 224 except for the gap in the annular sealing ring 224 defining the resistance window 225. During inhalation, fluid flows through the central opening 274 and out the lips of the valve member 279. Also, the exhalation flange 286 flexes toward the proximal end of the mouthpiece and provides a secondary seal against the outer ridge 288 inside the mouthpiece. The outer ridge 288 is preferably continuous around the inner circumference of the mouthpiece. Upon exhalation, the lips of the valve member 279 close, the exhalant passes through the resistance window under the upper portion 282 of the valve seat positioned adjacent the resistance window opening, and the exhalation flange flexes away from the outer ridge 288 and out between the aerosol holding chamber 214 and mouthpiece 216.

As shown in FIGS. **22*a*–22*c*, an embodiment of an apparatus 310 for performing PEP therapy is disclosed that may be used with or without an aerosol delivery apparatus. In contrast to the embodiments discussed above, the PEP apparatus of FIGS. 22*a*–22*c* is a standalone PEP device in a mouthpiece incorporating the previously discussed continuous variable resistance window with slide control, and variations thereof, along with a self contained valve 378 that may be similar to that disclosed in the previous embodiments. Thus, the valve 378 need not be found on the outlet end of a separate chamber extension 314 but may be positioned on the distal end 330 of the mouthpiece. As best shown in FIGS. 22b–22c, the valve 378 may be an annular valve. The 378 is preferably retained toward the distal end 330 of the apparatus by a central baffle 385 supported by radial spokes 386. In one embodiment, the PEP apparatus 310 is formed of an attachable mouthpiece section 316 and a baffle section 317. The mouthpiece and baffle sections 316, 317 may be removably joined using snap-fit, threaded or other known attachment schemes. In another alternative embodiment, the mouthpiece and baffle sections 316, 317 may be integrally molded or welded shut to form a non-removable, unitary piece. An extended inlet 314, without any valves, may be used with the stand-alone PEP device 310** to enhance delivery of any medicine to the patient's respiratory system. One function of the extended inlet is to provide a chamber for the dispensed particles from the pressurized metered dose inhaler. When desired, a pressurized metered dose inhaler may be coupled to the extended inlet with a backpiece and medicament supplied from the pressurized metered dose inhaler can be delivered directly to the user.

Although the embodiments of FIGS. 1–22 illustrate annular and duck-bill valves 24, 124, 278, 378, any of a number of other valve configurations may be used. A preferred valve is capable of passing a fluid moving in a first direction along a first path and also capable of passing a fluid moving in an opposite direction along a second path. In the example valves discussed above, inhalation draws fluid through a central opening in the valve while the perimeter of the valve prevents fluid flow. In the above examples, exhalation closes the path through the central opening and directs fluid along a second path around the perimeter of the valve. Other paths may also be used.

Figure 23:
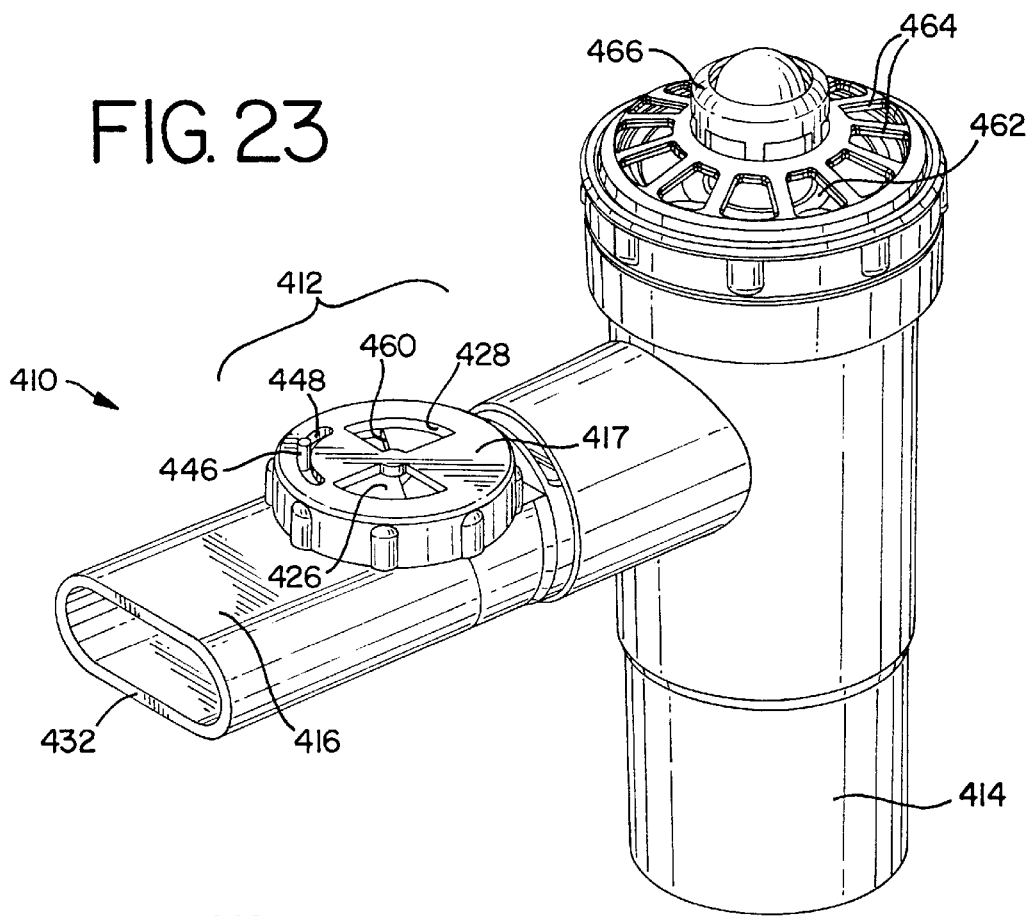
FIG. 23 is a perspective view of one embodiment of a PP apparatus in association with a nebulizer.
Figure 24:
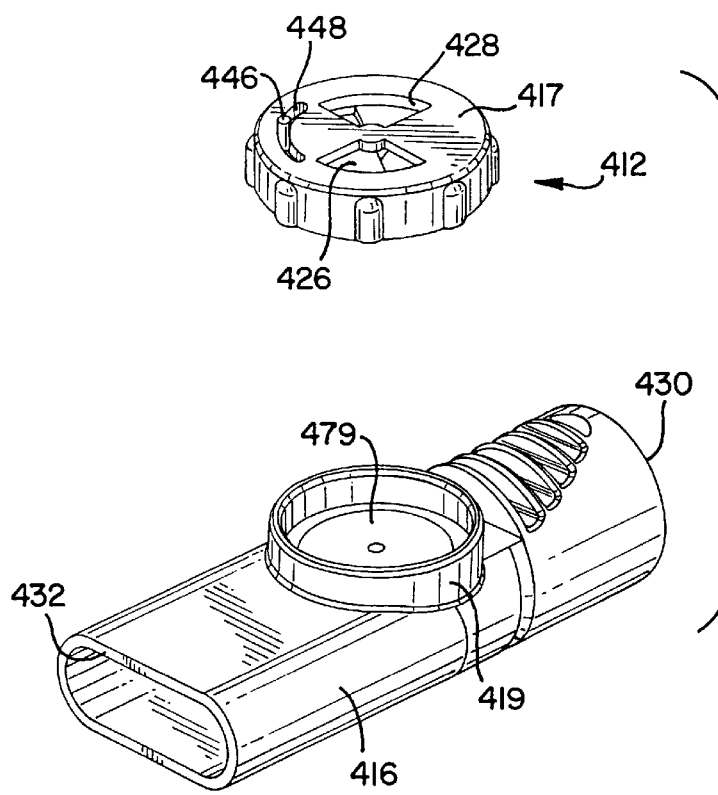
FIG. 24 is an exploded view of one embodiment of the PP apparatus and a mouthpiece.
Figure 25:
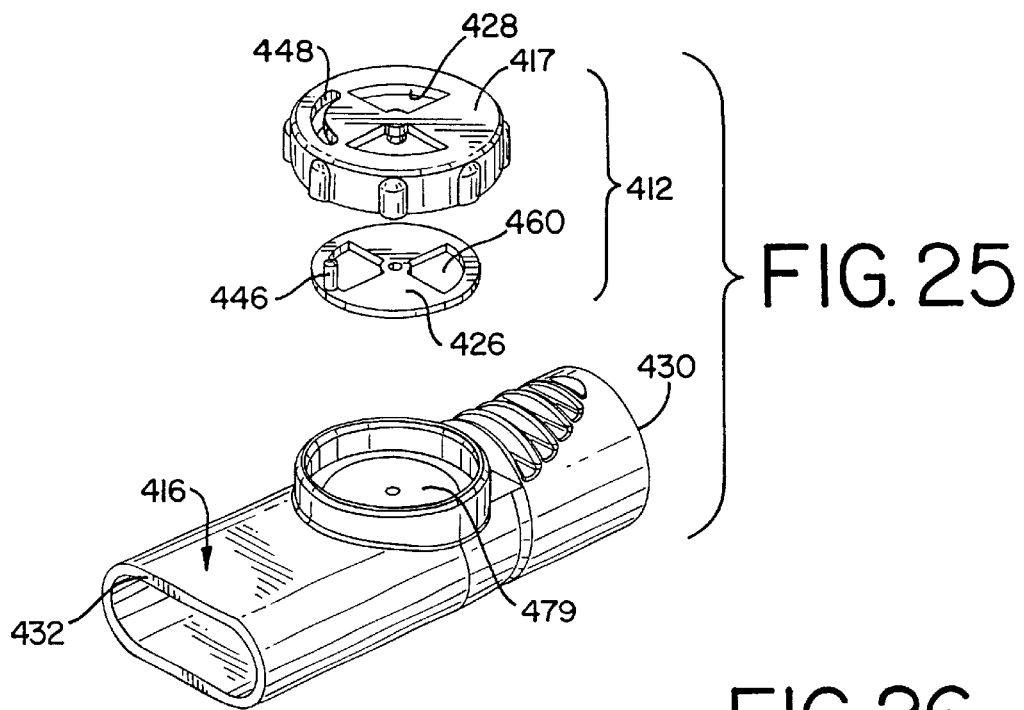
FIG. 25 is a perspective view of one embodiment of the PP apparatus in an open position and a mouthpiece.
Figure 26:
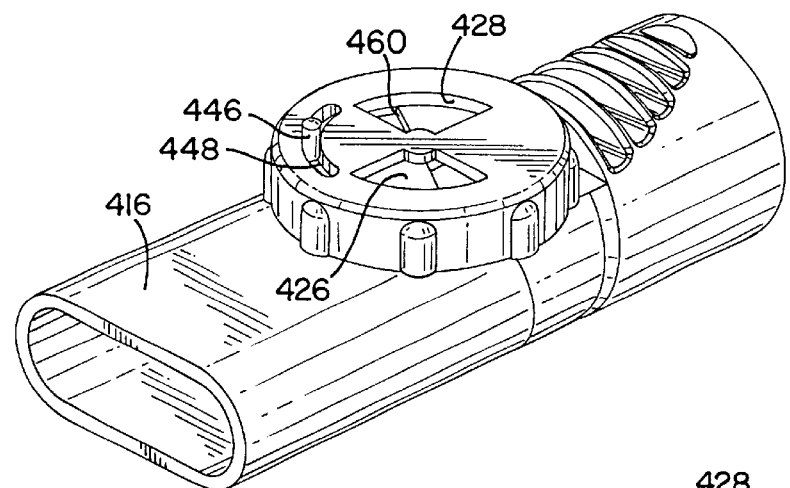
FIG. 26 is a perspective view of one embodiment of the PP apparatus in a semi-open position and a mouthpiece.
Figure 27:
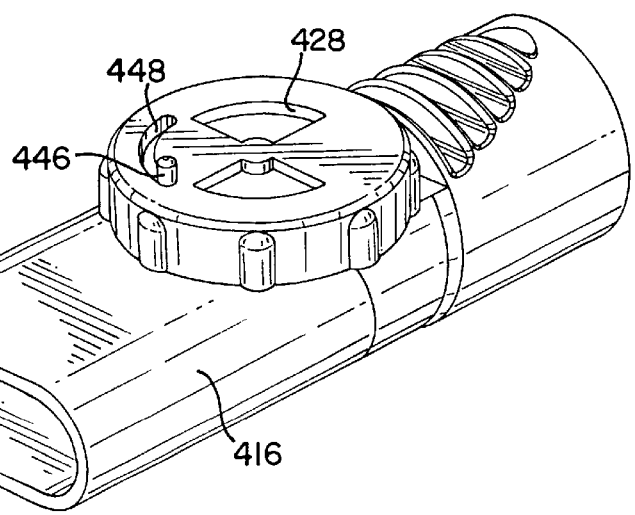
FIG. 27 is an exploded view of one embodiment of the PP apparatus showing the disc and a mouthpiece.
Figure 28A:
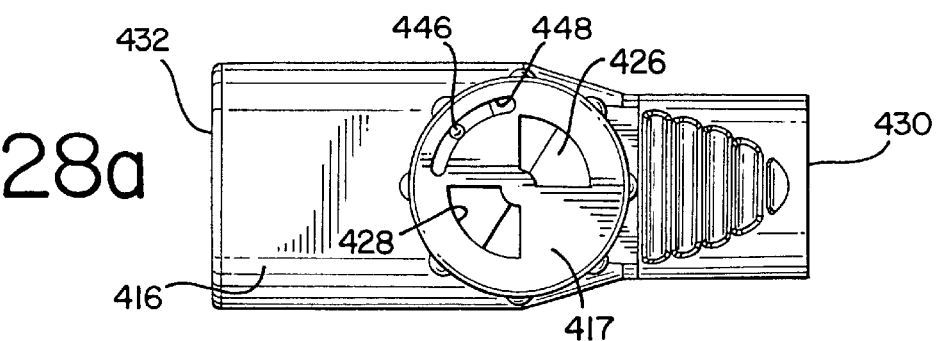
FIG. 28a is a top view of one embodiment of the PP apparatus and a mouthpiece.
Figure 28B:
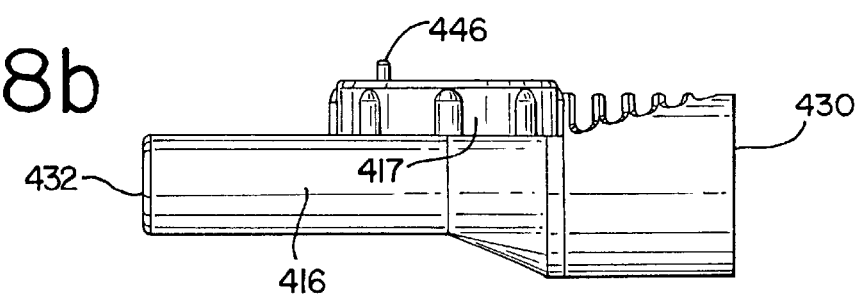
FIG. 28b is a cross section of one embodiment of the PP apparatus and a mouthpiece showing a plurality of prongs holding the PP apparatus.

FIGS. 23–28 illustrate another embodiment of a PEP apparatus 410. As best shown in FIG. 23, the PEP apparatus 410 has a patient respiratory system interface, such as a mouthpiece 416, on a proximal end 432 and may be connected with an aerosol delivery apparatus, in this example a nebulizer 414, at a distal end 430. The PEP apparatus includes a PP valve 412 positioned on top of the mouthpiece 416. The PP valve 412 preferably consists of a cover 417 that may be removably attached to a receiving area 419 (FIG. 24) on the mouthpiece 416. The cover has a resistance window 428 and a tab window 448 extending through a top surface. A slide control 426 in the form of a disk with vents 460 extending through the thickness of the disk is movably positioned under the cover 417. A one-way valve 423 is positioned between the slide control 426 and the top of the mouthpiece 416 to allow air exhaled into the proximal end 432 to escape through the resistance window 428 while preventing any air from entering through the resistance widow during inhalation.

In FIGS. 23–28, the resistance window 428 is shown generally as a pie-slice shaped cut-out with the point of the pie-slice removed so as to form a concave edge. The resistance window 428 may be any shape and should not be limited by the illustrated embodiment. Further, a plurality of resistance windows 428 may form the PP valve 412. The number of windows 428 is not intended to be limited by the illustrated embodiment. In the illustrated embodiment of FIGS. 23–28, and particularly FIG. 27, the slide control 426 is shown as a circular disc having a pie-slice shaped cut-outs with the point of the pie-slice openings therein which correspond to the openings of the resistance window 428. In operation, aligning the openings 460 of the disc with the resistance window 428 controls the opening of the continuously variable resistance window 428. When the resistance windows 428 are aligned with the disc openings 460, the resistance windows 428 are opened to their fullest extent allowing the resistance of the exhalant exiting the PP valve 412 to be lower. When only a small amount of the resistance windows 428 are aligned with the disc openings 460, the resistance of the exhalant exiting the PEP apparatus 410 is increased. By moving the tab setting 446 in the tab window 448, the vents may be adjusted in the disk 417 to any of a number of positions, thereby providing a continuously adjustable resistance. In this manner, positive expiratory pressure is controlled.

Referring again to FIG. 23, where the PEP apparatus 410 is connected at its distal end to the nebulizer 414, the operation of this embodiment will be described. Upon inhalation, the nebulizer will provide an aerosol to the inhaling patient via the mouthpiece. A suitable nebulizer for use with the PEP apparatus 410 is a breath-actuated nebulizer such as disclosed in U.S. Pat. No. 6,044,841 issued Apr. 4, 2000 and entitled "Breath Actuated Nebulizer with Valve Assembly Having Relief Piston", the entirety of which is incorporated herein by reference. During inhalation from the nebulizer 414, a piston 452 is drawn down by negative pressure created by the inhalation in the nebulizer and ambient air is drawn through openings 454 in the lid 456 of the nebulizer 414. The one-way valve 459 in the PP valve assembly 412 remains shut during inhalation.

Figure 29:
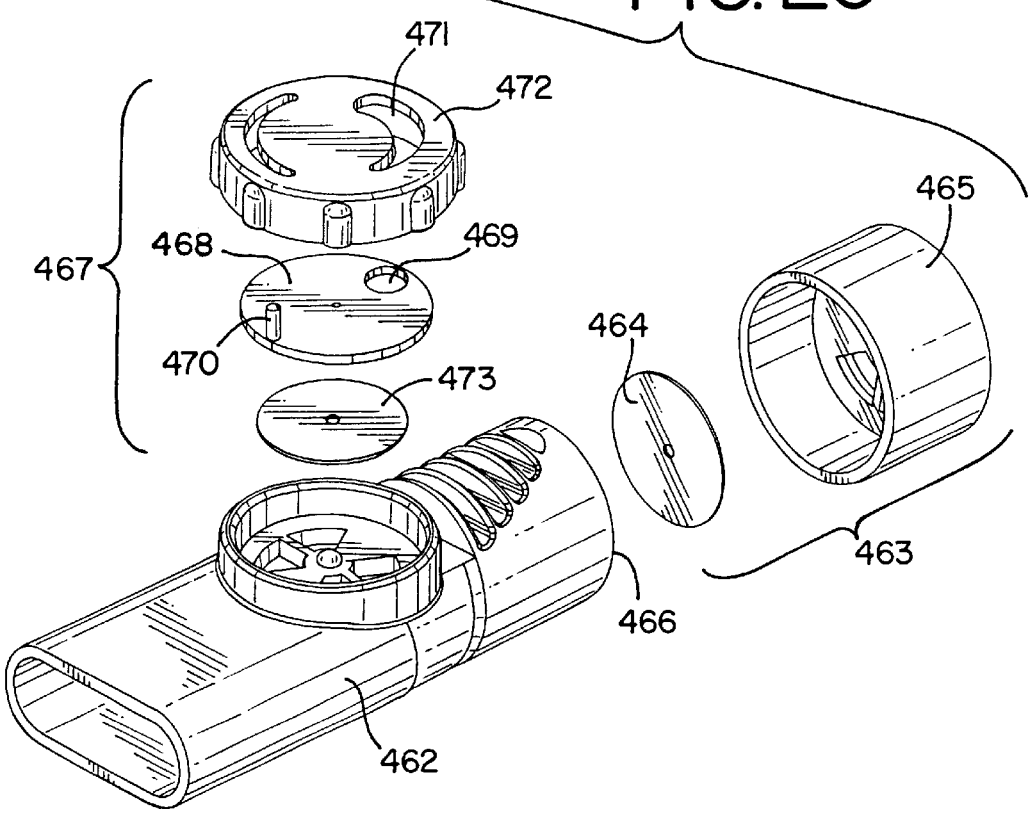
FIG. 29 is an exploded view of a PP apparatus associated with a mouthpiece and having an inhalation valve.

Upon exhalation into the proximal end 430 of the mouthpiece 416, a positive pressure builds in the nebulizer 414 and the piston acts as a one-way valve to close off the flow of air out of the nebulizer. Now, the exhalant must travel through the one-way valve in the PP valve assembly 412, through the slide control and out the resistance window. Preferably the slide control 426 under the resistance window 428 has been set to the appropriate position for the patient so that effective PEP therapy may be provided. Although the PEP apparatus of FIGS. 23–27 uses an aerosol delivery apparatus such as the nebulizer 414 to restrict air flow through any opening other than the PP valve assembly 412, other embodiments, such as shown in FIG. 29 discussed below, are contemplated where a second one-way valve is associated with the distal end 432 of the PEP apparatus 410 so that the PEP apparatus may be used in a standalone fashion for PEP therapy. The illustrated embodiment of FIGS. 23–28 show an improved nebulizer 414 associated with a PEP apparatus 410 having a PP valve 412. The nebulizer may be used alone or in combination with a mouthpiece mounted PP valve 412 or mask mounted version of the PP valve discussed below.

FIG. 29 shows an alternative embodiment of the PEP apparatus 410 of FIGS. 23–28 that may be used alone or coupled to a nebulizer or other aerosol delivery apparatus. As shown in FIG. 29, the mouthpiece 462 is provided with a one-way inhalation valve assembly 463 having a membrane 464 captured in an outlet cover 465 attached to the distal end 466 of the mouthpiece. The flexible membrane preferably covers vents in the outlet cover 465 during exhalation and flexes to allow fluid flow during inhalation. As with the embodiment of FIGS. 23–28, a PP valve assembly 467 is positioned on top of the mouthpiece. The PP valve assembly 467 differs from the PP valve assembly 412 in FIGS. 23–28 in that the slide control 468 contains a circular opening 469 that is moved by the tab setting 469 under a tear-drop shaped resistance window 471 in the cover 472. The inhalation valve 463 allows for fluid to enter the mouthpiece 462 but prevents fluid from exiting the mouthpiece. The exhalation valve 473 allows for exhalation through the resistance window 471 but prevents inhalation of particles or fluid. When assembled, a gap is presented between the exhalation valve 402 and the disc 56 in order to allow the exhalation valve 402 to open upon exhalation. In this manner, the mouthpiece 462 is adapted to be used alone and not in conjunction with a nebulizer or other aerosol delivery apparatus.

Although positive expiratory devices have been shown in detail, embodiments of positive inspiratory devices are also contemplated. FIG. 30 shows one embodiment, similar in concept to the embodiment of FIG. 29, but with the PP valve 475 attached in series with the one-way inhalation valve 476, rather than in series with the one-way exhalation valve, to provide for resistance upon inhalation only. The arrows drawn in FIG. 30 depict the direction of travel from the downstream end of the mouthpiece 478 to the upstream end of the mouthpiece showing that all inhalation must pass through the continuous variable resistance window 480 and the port 482 of the slide control 484. If desired, in other embodiments PP valves may be placed in series with both the one-way input and one-way output valves to allow for simultaneous control of positive inspiratory and expiratory pressures at the same or different levels.

As discussed above, embodiments of patient respiratory system interfaces aside from the mouthpiece configurations already disclosed are contemplated. A PP apparatus 510 utilizing a mask 512 as the interface is illustrated in FIGS. 31–35. The mask may be a standard mask sized for adults or children and constructed of any of a number of materials such as silicon rubber. The mask 512 may have a frusto-conical shaped main section 514 sized to cover the patient's mouth and a nosepiece section 516 sized to cover a patient's nose. A central opening 518 in the mask 512 may be used to attach with an aerosol delivery apparatus such as the aerosol holding chamber 14 shown in FIGS. 1–3, and other aerosol delivery apparatus. Alternatively, the mask 512 may be fitted with a one-way valve in the central opening 518 for use as either a positive expiratory pressure device or a positive inspiratory pressure device. As with the embodiment of FIGS. 23–28 and 29–30, a PP valve assembly 520 is positioned on the device so that inspiration and exhalation paths travel off-axis from one another. The PP valve assembly 520 has an adjustable valve assembly cover 534 with tab window 522 and resistance window 528 openings positioned on it. The resistance window 528 is generally an oblong, tear-drop shape and the tab window 522 defines an arcuate opening in the PP valve cover 534. The tab window and resistance window may alternatively be rectangular, oval or any other shape. Although the above embodiments illustrate a tab window 522 located approximately on a top surface of a mouthpiece or on top of a mask positioned approximately adjacent the nose, the tab window 522 may be located anywhere on the mouthpiece or mask.

Referring to FIGS. 35a and 35b, the PP valve assembly 520 has a fixed opening 530 and a set of detents 532 positioned on a disk-shaped platform 526 that connects to the nosepiece section of the mask through complementary tab 542 and slot 544 connectors. As best shown in FIG. 35b, the PP valve cover 534 has a protrusion 536 sized to cooperate with the detents 532 on the platform 526 so that the valve cover may be moved to predetermined spots when the valve cover is rotated against the platform. An axle 538 on the valve cover fits into a central opening 540 in the platform 526 so that the resistance window 528 is rotatably positionable over the exhalation port 530 and the tab window 522 lines up with the tab extending from the platform 526.

This embodiment depicts the resistance window 528 as a curved tear-drop like shape. The platform 526 is shown as a circular disc having at least one port opening 530. The port opening 530 may vary in size and shape. The opening formed for the exhalant to pass through is related to the alignment of the resistance window 528 with the port opening 530. In this embodiment, the resistance window is moveably mounted relative to a fixed slide control portion attached to the mask. Tabs 542 on the platform 526 preferably mate with tab receiving regions 544 on the end of the nosepiece extension 516 to retain the platform in a fixed position relative to the mask. Moving the tear-drop shaped resistance window 528 past the port opening 530 varies the exhalant path. In other embodiments, a plurality of resistance window openings 528 may be moved past the port 530. Alternatively, there may be a plurality of ports in the slide control 526.

Figure 32A:
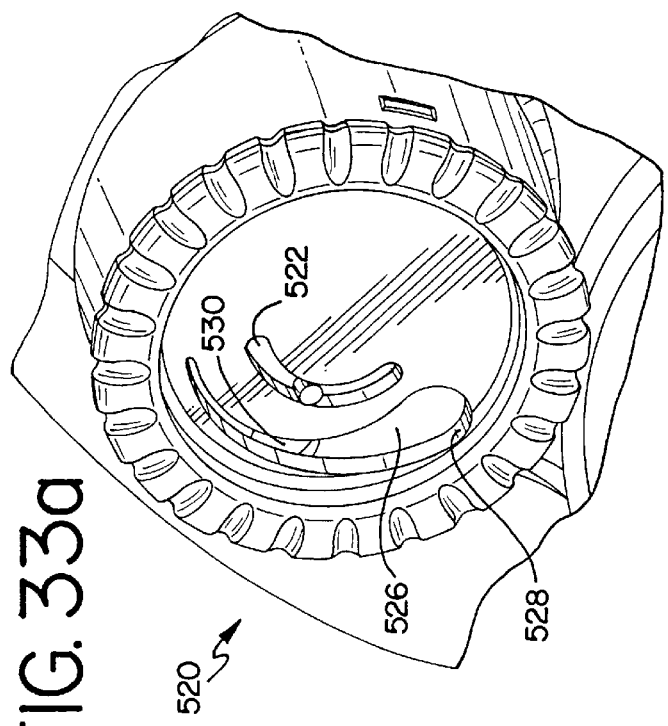
FIG. 32a is a close up of one embodiment of the PP apparatus in a fully open position in conjunction with a mask.
Figure 32B:
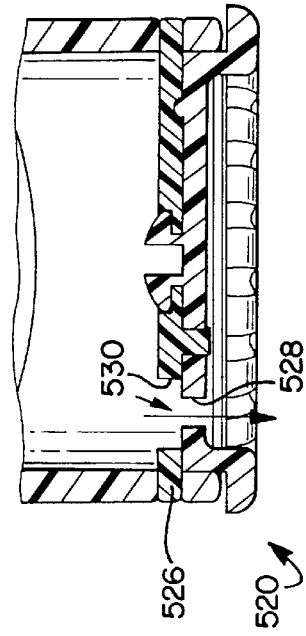
FIG. 32b is a cross section of one embodiment of the PP apparatus in a fully open position in conjunction with a mask.
Figure 33A:
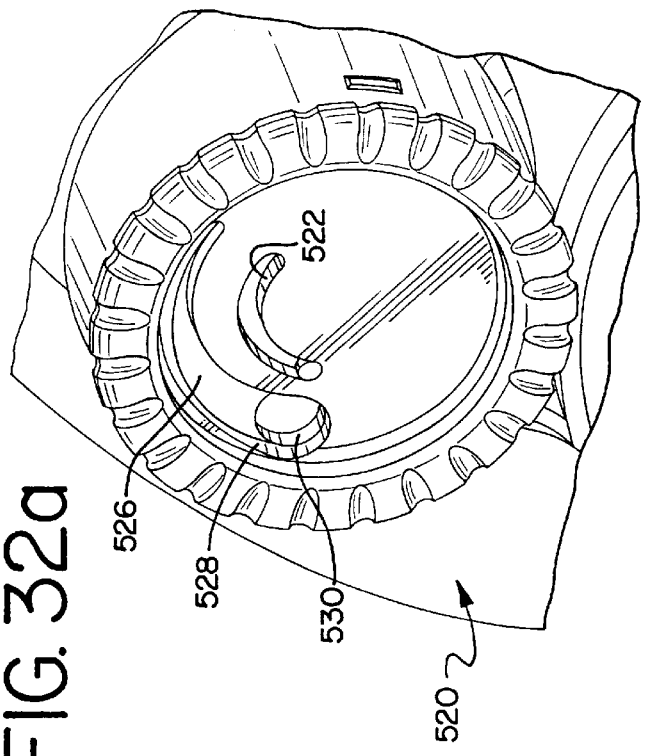
FIG. 33a is a close up of one embodiment of the PP apparatus in a partially open position in conjunction with a mask.
Figure 33B:
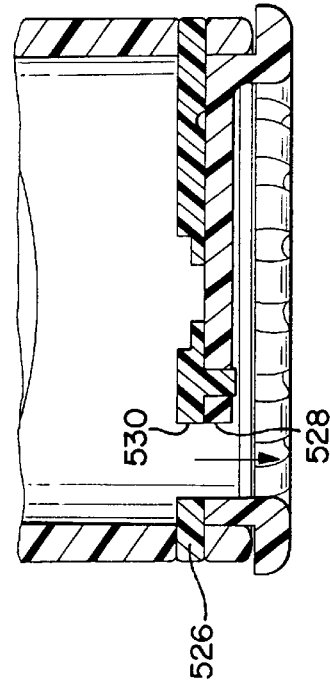
FIG. 33b is a cross section of one embodiment of the PP apparatus in a partially open position in conjunction with a mask.
Figure 36:
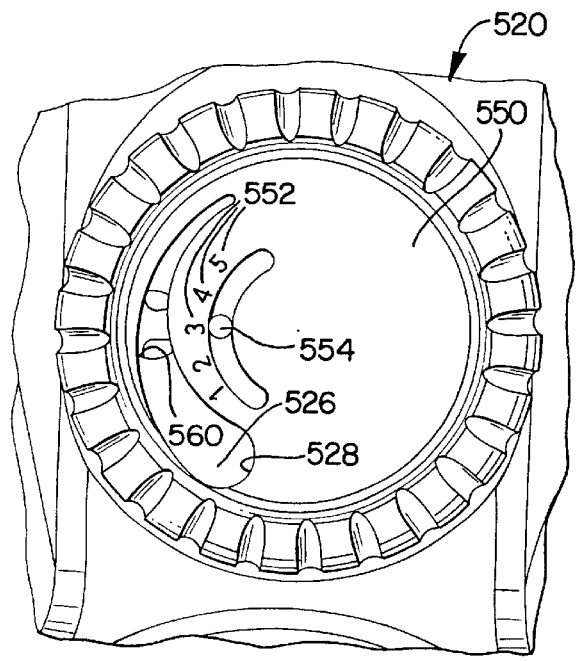
FIG. 36 is a front view of one embodiment of the PP apparatus showing resistance setting indicia.

As shown in FIGS. 31 and 32a, one end of the tear-drop shaped resistance window 528 matches the size of the largest port opening 530 at a maximum flow position thereby providing a maximum flow and least resistance in that position. When the valve cover is rotated so that the resistance window 528 covers a greater portion of the port, as shown in FIGS. 33a–33b, a smaller exhalant path is created providing greater resistance. As shown in FIGS. 34a–34b, moving the valve cover until the tab reaches the opposite end of the tab window results in the smallest amount of the port being open, the highest airflow resistance and the least flow. It is envisioned that a plurality of size and shape port openings and resistance windows may be used and the disclosure is not to be limited to that depicted in the drawings. Referring to FIG. 36, an embodiment is shown of a valve cover 550 having indicia 552 representative of a resistance setting. The indicia 552 are arranged to cooperate with the tab extension 554 on the platform to indicate the current resistance setting.

In alternative embodiments, PEP therapy may be performed with a mouthpiece or mask having the PP valve associated with a backpiece. The mask or mouthpiece may have an extended inlet for association with the backpiece.

Asthmatic medications are commonly supplied in metered dose inhalers, frequently referred to as pressurized metered dose inhalers. Pressurized metered dose inhalers are generally cylindrical canisters with axially extending vent tubes from internal valves. When the external tube or stem of a pressurized metered dose inhaler canister is depressed it operates the internal valve to dispense a measured dose of medicine from the stem. The medicine is commonly packed in the canister with a suitable compressed gas to propel the medicine and gas from the stem or tube when the later is depressed. The medicine may be in gas, liquid, or solid form. The manufacturer or distributor of the pressurized metered dose inhaler canister generally supplies it with a substantially L-shaped adapter which receives the canister in a substantially upright position, and has a substantial horizontal outlet portion for reception in the mouth of an asthmatic patient for inhalation of the medicine.

In order to address the problem of coordination and other problems known in the art with regard to pressurized metered dose inhalers, a spacer chamber with an integrated actuator, or an aerosol holding chamber, have been used in attempts to overcome inappropriate particle size. The aerosol holding chamber is generally provided at the upstream or entering end with a flexible, resilient adapter or backpiece made of rubber or the like material. A central aperture is provided for receipt of the horizontal outlet portion of the pressurized metered dose inhaler adapter.

Figure 37:
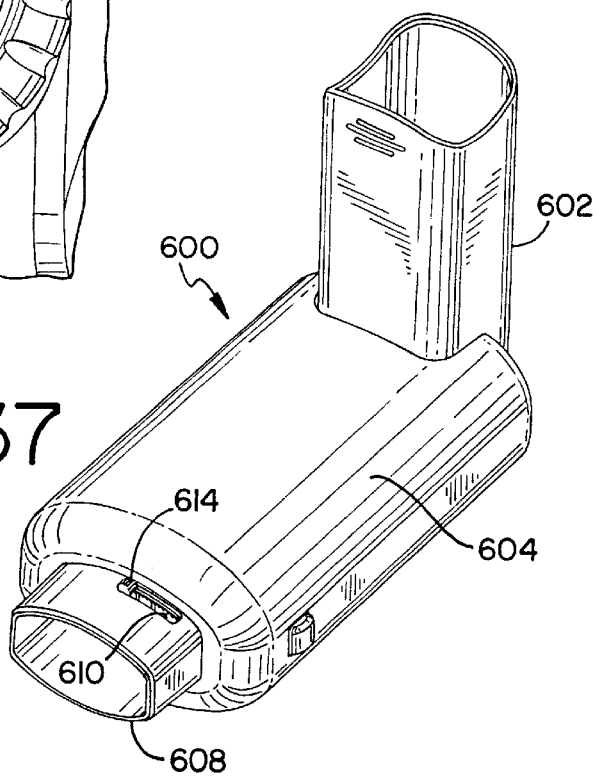
FIG. 37 shows a perspective view of a spacer for a pressurized metered dose inhaler with one embodiment of the PP apparatus.
Figure 38A:
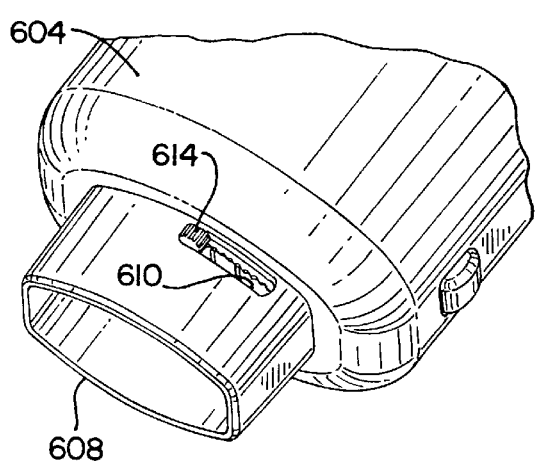
FIG. 38a is a perspective view of one embodiment of the resistance window in the open position.
Figure 38B:
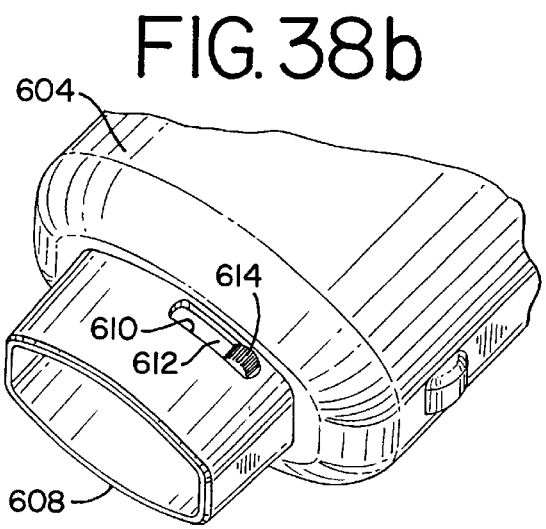
FIG. 38b is a perspective view of the embodiment of FIG. 38a with the resistance window in a closed position.
Figure 39A:
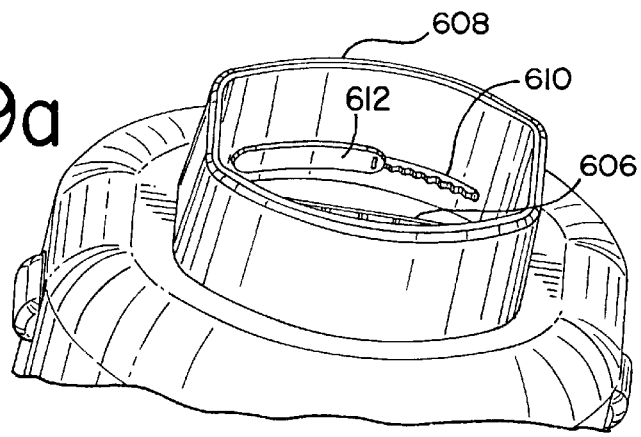
FIG. 39a is a perspective view of one embodiment of the resistance window in the open position.
Figure 39B:
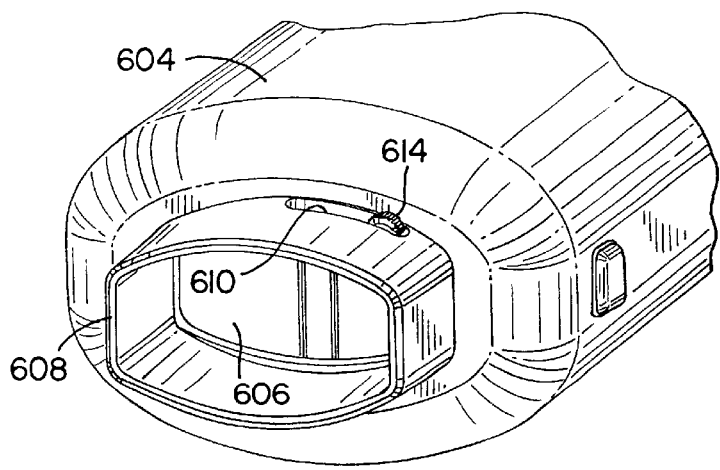
FIG. 39b is a perspective view of one embodiment of the resistance window in the closed position.
Figure 40:
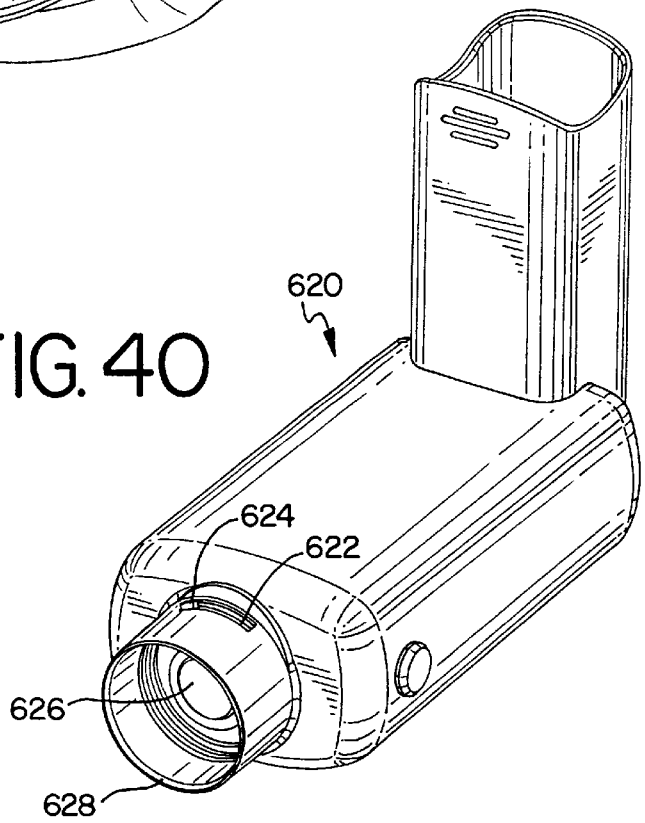
FIG. 40 illustrates an alternative embodiment of the apparatus of FIGS. 37–39.

One embodiment provides for an improved pressurized metered dose inhaler or pressurized metered dose inhaler with an aerosol holding chamber. As shown in FIG. 37, a PP apparatus 600 may be associated with the pressurized metered dose inhaler or the pressurized metered dose inhaler with an aerosol holding chamber. In the PP apparatus 600 of FIGS. 37–39, an L-shaped adapter portion 602 holds the pressurized canister and a horizontal outlet section 604 receives the medicament released in aerosol form. A one-way valve 606, which may be a flexible membrane, a rigid membrane, hinged door, or other commonly known valve mechanism is positioned at the proximal end 608 of the horizontal outlet section 604. To provide the positive expiratory pressure, the one-way valve 606 permits inhalation and blocks exhalation so that substantially all exhalation is routed through the variable resistance window 610 adjacent the one-way valve 606. A slide control 612 is movable in the resistance window 610 by a tab 614 to close off or open up as much of the resistance window as necessary to provide the desired expiratory pressure. FIGS. 38a and 39a illustrate the slide control in a completely open position and FIGS. 38b and 39b illustrate the slide control closing off the resistance window. The slide control may maintain its position in the resistance window through friction, detents or other known mechanisms for mechanically retaining one of multiple desired positions. The proximal end 608 of the metered dose inhaler 600 with PP functionality may be used by a patient directly or fitted to an adapter on an aerosol chamber such as shown in FIG. 3. FIG. 40 illustrates another embodiment of a pressurized metered does inhaler 620 with a round proximal end 628 that may be used without the need for special mouthpieces or aerosol holding chambers. As with the embodiment of FIGS. 37–39, the alternative PEP enabled pressurized metered dose inhaler 620 has a one-way valve 626 that shunts exhalant through a resistance window 622 that is continuously adjustable with a slide control 624 that can adjust the aperture of the resistance window.

Generally, a mouthpiece or mask may be associated the PP apparatus. In one configuration, an aerosol holding chamber may be attached to the mouthpiece or mask end and a metered dose inhaler may be positioned on a generally opposite end of the chamber via a backpiece. The user of the device may insert the mouthpiece into the mouth to obtain a dose of medicament. Further, the user may place the mask over the mouth and/or nose to inspire a dose of the medicament. In either situation, the mask or mouthpiece aids in the delivery of the medicament to the user.

As has been described, a method and apparatus from providing positive expiration or inhalation therapy, with or without separate aerosol generating devices, has been disclosed. In the embodiment where the positive expiratory pressure valve is located at or near the output end of the aerosol delivery apparatus, a one way inhalation valve can be located further downstream from the positive expiratory pressure valve. A mouthpiece and or mask can be affixed at or near the output end of the aerosol delivery apparatus. The positioning of the inhalation valve either upstream or downstream in respect to the positive expiratory pressure valve is well known to one skilled in the art. Further, it is envisioned that PEP therapy may be performed nasally with the positive expiratory pressure apparatus.

When the mouthpiece having the PP apparatus associated therewith is used alone to perform PEP therapy, and not in conjunction with a mechanism for the delivery of a substance, a one way inhalation valve is engageable with the mouthpiece. The inhalation valve functions so as to allow for inhalation by the patient into the mouthpiece. The exhalant of the patient is prevented from exiting via the inhalation valve and is directed to exit through the PP valve. Generally, an inhalation valve opens upon inhalation to allow a fluid, such as an aerosol, to enter a chamber or channel or the like but that closes upon exhalation to prevent exhaled fluids to enter into the chamber of the like. The drawings depict an exemplary embodiment of the one-way inhalation valve but are not to be limiting to the embodiments shown.

One aspect of the method of use of the PP apparatus can be understood by the following disclosure and reference to FIGS. 1–3, 5 and 9. Particularly, the arrow 2 in FIG. 1 indicates the direction of flow of the exhalant. The one-way valve shunts exhalant out between the mouthpiece and the aerosol chamber via the continuously variable resistance window. In carrying out the method, a physician may initially determine the proper resistance setting of the PP apparatus according to the patient's requirements. One manner in which the PP apparatus may be properly set is by attaching a fitting 39 to the mouthpiece. A manometer is then attached to the fitting port 41 and serves to measure the expiratory pressure. A patient will exhale into the mouthpiece and the pressure can be read from the manometer. The physician can the move the tab to one of the desired settings indicated on the mouthpiece. Once the proper resistance has been determined the fitting 39 can be removed from the mouthpiece. This fitting 39 will not be used again unless it is determined that the resistance should be adjusted.

The method of performing PEP therapy using the PP apparatus includes performing a series of breaths. When exhalation is performed, the exhalant is directed through the continuously variable expiratory window. Performance of a therapeutic cough triggers the loosening of secretions. Upon loosening of the secretions, a medicament may be provided for inhalation into the respiratory system. In one embodiment of PEP therapy, the user will exhale into the mouthpiece and/or mask, against the desired resistance. This is done either prior to or in combination with inhalation of the medicament. The exhaled gases exit through the resistance window. This process may be repeated as many times as prescribed by the patient's physician.

As has been described, a method and apparatus for providing positive expiration, or inhalation, pressure therapy, with or without separate aerosol generating devices, has been disclosed. The aerosol delivery apparatus with the PP apparatus may be used alone or in combination with a mask or mouthpiece. Also, an improved aerosol delivery apparatus with an integrated actuator has been shown, wherein the improvement comprises a PP valve. The discussion above is descriptive, illustrative and exemplary and is not to be taken as limiting the scope defined by any appended claims.

What is claimed is:

1. A positive respiratory pressure apparatus comprising:
a patient respiratory system interface; and
a valve assembly in fluid communication with the patient respiratory system interface, the valve assembly comprising:
a valve configured to pass a fluid traveling in a predetermined direction from a first side to a second side of the valve; and
a variable resistance bypass window positioned adjacent the valve and having a resistance to a fluid traveling in a direction opposed to the predetermined direction, wherein the variable resistance bypass window is continuously adjustable between a first fluid resistance and a second fluid resistance.

2. The apparatus of claim 1, wherein the valve comprises a one-way inhalation valve portion, the one-way inhalation valve portion providing an inhalation path and preventing exhalation along the inhalation path.

3. The apparatus of claim 2, wherein the valve further comprises a one-way exhalation valve portion, the one-way exhalation valve portion providing an exhalation path and preventing inhalation along the exhalation path, wherein the exhalation path is different than the inhalation path.

4. The apparatus of claim 3, wherein the valve comprises a duck-bill valve comprising an open central region and a central valve member, wherein the open central region and the central valve member define the inhalation path, and wherein the duck-bill valve further comprises a peripheral exhalation flange defining the exhalation path.

5. The apparatus of claim 1, wherein the valve comprises a one-way valve.

6. The apparatus of claim 1, wherein the valve comprises a one-way inhalation valve.

7. The apparatus of claim 1, wherein the valve comprises a one-way exhalation valve.

8. The apparatus of claim 1, wherein the fluid traveling in the predetermined direction comprises inhaled gas.

9. The apparatus of claim 1, wherein the fluid traveling in the predetermined direction comprises exhaled gas.

10. The apparatus of claim 1, wherein the patient respiratory system interface comprises a mouthpiece.

11. The apparatus of claim 1, wherein the patient respiratory interface comprises a mask.

12. The apparatus of claim 1, wherein the valve comprises an annular valve.

13. The apparatus of claim 1, wherein the valve comprises a duck-bill valve.

14. The apparatus of claim 1, wherein the variable resistance bypass window comprises first and second overlapping apertures continuously positionable relative to one another between a first position, where the first and second overlapping apertures align to provide a maximum opening between the patient respiratory system interface and ambient air outside of the patient respiratory system interface, and a second position, where the first and second apertures cooperate to provide a minimum opening between the patient respiratory system interface and ambient air outside of the patient respiratory system interface.

15. The apparatus of claim 14 wherein the first overlapping aperture comprises a fixed opening in the patient respiratory system interface that is fixed relative to the patient respiratory system interface and the second overlapping aperture comprises a movable control portion defining a movable opening that is continuously adjustable to overlap with the fixed opening.

16. The apparatus of claim 15, wherein the fixed opening is positioned over the movable opening.

17. The apparatus of claim 15, wherein the fixed opening is positioned beneath the movable opening.

18. The apparatus of claim 14, wherein the valve is positioned to permit inhalation and restrict exhalation, wherein an exhalation flows through the variable resistance bypass window.

19. The apparatus of claim 16, wherein the fixed opening comprises an opening in a circular wall formed in the patient respiratory interface, and the control portion comprises a strip of material movably positioned adjacent the opening in the circular wall.

20. The apparatus of claim 19, wherein the movable opening defined by the strip of material comprises a variable height portion of the strip of material, the variable height portion having a continuously sloping height ranging from a first height that is at least as high as a height of the circular wall, to a second height that is less than the height of the circular wall.

21. The apparatus of claim 20, wherein the strip of material is an arcuate strip of material.

22. The apparatus of claim 19, wherein the movable opening defined by the strip of material comprises a variable width opening in at least a portion of the strip of material, the variable width opening having a continuously changing width from a first position to a second position along a length of the strip.

23. The apparatus of claim 22, wherein the strip of material is an arcuate strip of material.

24. The apparatus of claim 1, wherein the valve comprises a one-way inhalation valve, and wherein the apparatus further comprises a discrete one-way exhalation valve mounted independently of the one-way inhalation valve.

25. A positive respiratory pressure apparatus comprising:
a patient respiratory system interface;
an aerosol delivery apparatus in fluid communication with the patient respiratory system interface; and
a valve assembly in fluid communication with the patient respiratory system interface, the valve assembly comprising:
a valve configured to pass a fluid traveling in a predetermined direction from a first side to a second side of the valve; and
a variable resistance bypass window positioned adjacent the valve and having a resistance to a fluid traveling in a direction opposed to the predetermined direction, wherein the variable resistance bypass window is continuously adjustable between a first fluid resistance and a second fluid resistance.

26. The apparatus of claim 25, wherein the valve assembly is in fluid communication with both the patient respiratory system interface and the aerosol delivery apparatus.

27. The apparatus of claim 25, wherein the aerosol delivery apparatus comprises a nebulizer.

28. The apparatus of claim 25, wherein the aerosol delivery apparatus comprises a metered dose inhaler.

29. The apparatus of claim 25, wherein the aerosol delivery apparatus comprises an aerosol holding chamber.

30. The apparatus of claim 25, wherein the valve comprises a one-way valve and is positioned between the aerosol chamber and the patient respiratory system interface to permit inhalation through the aerosol chamber and prevent exhalation through the aerosol holding chamber.

31. The apparatus of claim 30, wherein the one-way valve comprises a duck-bill valve.

32. A method of performing positive expiratory pressure therapy in combination with providing an aerosolized medicament, the method comprising:
providing a positive expiratory pressure apparatus, the positive expiratory pressure apparatus comprising a positive expiratory pressure valve having a continuously variable resistance exhalation window, where the valve is positionable in a mouthpiece attached with an aerosol holding chamber;
performing a series of therapeutic breaths, comprising inhalation and exhalation, wherein exhalant is directed through the continuously variable resistance window;
providing a variable back pressure to the exhalant with the continuously variable resistance window;
triggering the loosening of sections with a therapeutic cough; and
inhaling an aerosolized medicament from the aerosol holding chamber.

* * * * *